(12) United States Patent
Krebbers et al.

(10) Patent No.: US 7,572,951 B2
(45) Date of Patent: Aug. 11, 2009

(54) PLANT VIRAL MOVEMENT PROTEIN GENES

(75) Inventors: Enno Krebbers, Ardentown, DE (US); Zude Weng, Des Plaines, IL (US); Rebecca E. Cahoon, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/653,567

(22) Filed: Jan. 16, 2007

(65) Prior Publication Data

US 2007/0186309 A1    Aug. 9, 2007

Related U.S. Application Data

(62) Division of application No. 09/913,569, filed as application No. PCT/US00/09110 on Apr. 6, 2000, now Pat. No. 7,186,885.

(60) Provisional application No. 60/128,092, filed on Apr. 7, 1999.

(51) Int. Cl.
*A01H 5/00* (2006.01)
*A01H 5/10* (2006.01)
*C12N 15/29* (2006.01)
*C12N 15/82* (2006.01)

(52) U.S. Cl. .............. 800/279; 800/278; 800/298; 435/320.1; 435/419; 435/468; 536/23.1; 536/23.6

(58) Field of Classification Search .............. None
See application file for complete search history.

(56) References Cited

FOREIGN PATENT DOCUMENTS

WO    WO 97/07217 A1    2/1997
WO    WO 97/20470 A1    6/1997

OTHER PUBLICATIONS

GenBank Accession AAC35866 also GI: 3603473, Mar. 1, 1998.
Xoconostle-Cazares B. et al., Science, Jan. 1, 1999, vol. 23, pp. 94-98.
Almon E. et al., Plant Physiology, 1997, vol. 115, pp. 1599-1607.
Doerks et al., TIG, 1998, vol. 14, No. 6, pp. 248-250.
Smith T. et al., Nature Biotechnology, Nov. 1997, vol. 15, pp. 1222-1223.
Brenner S. et al., TIG, Apr. 1999, vol. 15, No. 4, pp. 132-133.
Bork P. et al., TIG, Oct. 1996, vol. 12, No. 10, pp. 425-427.
Venter C. et al., Science, 2001, vol. 291, pp. 1304-1351.
GenBank Accession AAC35866 also Gi: 3603473; Sep. 16, 1998.
NCBI, General Identifier No. 3603473, Sep. 16, 1998, Kim, C.Y., et al., Identification and Characterization of Fungal Elicitor Responsive Rice Genes by mRNA . . . .
NCBI, General Identifier No. 2911047, Mar. 10, 2000, Bevan, M. et al.
NCBI, General Identifier No. 2911073, Apr. 7, 1999, Bevan, M. et al.
NCBI, General Identifier No. 3860331, Nov. 11, 1998, Dopico, B. et al., cDNA expressed in chickpea epicotyis.
NCBI, General Identifier No. 1498055, Aug. 21, 1996, Betawar, N.M. et al., Novel maize gene.
EMBL Database Sequence Library Accession No. AF090698, Sep. 23, 1998, C.Y. Kim et al., Identification and Characterization of Fungal Elicitor Responsive . . . .
EMBL Database Sequence Library Accession No. AA556184, Aug. 3, 1998, I. Allona et al., Analysis of xylem formation in pine by cDNA sequencing.
EMBL Database Sequence Library Accession No. C73264, Sep. 22, 1997, Sakai, T. et al., Rice cDNA from panicle at flowering stage.
Cazares, B et al., Science 283:94-98, 1999, Plant Paralog to Viral Movement Protein That Potentiates Transport of mRNA Into the Phloem.
EMBL Database Sequence Library Accession No. AF079170, Jan. 20, 1999, B.C. Yoo et al., Plant paralog to viral movement protein that potentiates transport . . . .
EMBL Database Sequence Library Accession No. U95136, Mar. 10, 1998, C.Y. Kim et al, Isolation and characterization of early rice genes by a fungal elicitor . . . .
EMBL Database Sequence Library Accession No. U95135, Mar. 10, 1998, C.Y. Kim et al., Isolation and characterization of early rice genes by a fungal . . . .
EMBL Database Sequence Library Accession No. U64437, Aug. 23, 1996, N.M. Betawar et al., Novel Maize Gene.
David L. Beck et al., PNAS, vol. 91:10310-10314, 1994, Disruption of virus movement confers broad-spectrum resistance against systemic . . . .

*Primary Examiner*—Russell Kallis

(57) ABSTRACT

This invention relates to an isolated nucleic acid fragment encoding a viral movement protein. The invention also relates to the construction of a chimeric gene encoding all or a substantial portion of the viral movement protein, in sense or antisense orientation, wherein expression of the chimeric gene results in production of altered levels of the viral movement protein in a transformed host cell.

12 Claims, No Drawings

PLANT VIRAL MOVEMENT PROTEIN GENES

This application is a divisional of U.S. patent application Ser. No. 09/913,569 filed Aug. 13, 2001, which is a national stage entry of PCT/US00/09110 filed Apr. 6, 2000, which claims the benefit of U.S. Provisional Application No. 60/128,092, filed Apr. 7, 1999.

FIELD OF THE INVENTION

This invention is in the field of plant molecular biology. More specifically, this invention pertains to nucleic acid fragments encoding viral movement proteins in plants and seeds.

BACKGROUND OF THE INVENTION

The phloem of a plant is a vascular tissue that is responsible for distributing the products of photosynthesis, nutrients and hormones to plant tissues and organs. Associated with the phloem are sieve elements and companion cells. Mature sieve cells are enucleate and must rely on physically connected companion cells (via a branched plasmodesmata) to provide many physiological functions. Sieve cells and companion cells together serve to deliver proteins into the phloem. Research has shown that specific mRNA molecules can be found in the plasmodesmata suggesting that there are mechanisms that participate in mRNA transport through the sieve cell-companion cell plasmodesmata connection (Xoconostle-Cazares, B., et al., (1999) Science 283:94-98). Some plant viruses have been shown to be able to establish systemic infections via movement proteins (MP) that have the capacity to interact with the plasmodemata and foster the cell-cell transport of MP and viral nucleic acids. Thus plant viruses have evolved the capacity to utilize existing plant pathways to traffic macromolecules to surrounding cells. Plants appear to have proteins similar to viral movement proteins that function in the transport of nucleic acids from cell to cell. Several plant genes that encode viral movement protein homologs have been identified in rice (elicitor-responsive gene 3, Os-FIERG1 and Os-FIERG2), while one has been identified in corn (novel gene) and one has been identified in *Cucurbita maxima* (CmPP16) (Xoconostle-Cazares, B., et al., (1999) Science 283:94-98). Interestingly, movement of RNA throughout the plant is postulated by some to explain the phenomena of cosuppression. Thus, understanding plant viral movement protein homologs and how they work will provide mechanisms to control cosuppression and provide mechanisms to engineer plant virus resistance.

SUMMARY OF THE INVENTION

The present invention concerns an isolated polynucleotide comprising a nucleotide sequence selected from the group consisting of: (a) a first nucleotide sequence encoding a polypeptide of at least 129 amino acids having at least 95% identity based on the Clustal method of alignment when compared to a polypeptide selected from the group consisting of SEQ ID NOs:2, 4, 6, 8, 10, 12, 14, 16, 18, 20, 22, 24, 26, 28, 30 and 32, or (b) a second nucleotide sequence comprising the complement of the first nucleotide sequence.

In a second embodiment, it is preferred that the isolated polynucleotide of the claimed invention comprises a first nucleotide sequence which comprises a nucleic acid sequence selected from the group consisting of SEQ ID NOs: 1, 3, 5, 7, 9, 11, 13, 15, 17, 19, 21, 23, 25, 27, 29 and 31 that codes for the polypeptide selected from the group consisting of SEQ ID NOs:2, 4, 6, 8, 10, 12, 14, 16, 18, 20, 22, 24, 26, 28, 30 and 32.

In a third embodiment, this invention concerns an isolated polynucleotide comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13, 15, 17, 19, 21, 23, 25, 27, 29 and 31 and the complement of such nucleotide sequences.

In a fourth embodiment, this invention relates to a chimeric gene comprising an isolated polynucleotide of the present invention operably linked to at least one suitable regulatory sequence.

In a fifth embodiment, the present invention concerns a host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

In a sixth embodiment, the invention also relates to a process for producing a host cell comprising a chimeric gene of the present invention or an isolated polynucleotide of the present invention, the process comprising either transforming or transfecting a compatible host cell with a chimeric gene or isolated polynucleotide of the present invention.

In a seventh embodiment, the invention concerns a viral movement protein of at least 129 amino acids comprising at least 95% identity based on the Clustal method of alignment compared to a polypeptide selected from the group consisting of SEQ ID NOs:2, 4, 6, 8, 10, 12, 14, 16, 18, 20, 22, 24, 26, 28, 30 and 32.

In an eighth embodiment, the invention relates to a method of selecting an isolated polynucleotide that affects the level of expression of a viral movement protein or enzyme activity in a host cell, preferably a plant cell, the method comprising the steps of: (a) constructing an isolated polynucleotide of the present invention or a chimeric gene of the present invention; (b) introducing the isolated polynucleotide or the chimeric gene into a host cell; (c) measuring the level of the viral movement proteins polypeptide or enzyme activity in the host cell containing the isolated polynucleotide; and (d) comparing the level of the viral movement protein or enzyme activity in the host cell containing the isolated polynucleotide with the level of the viral movement protein or enzyme activity in the host cell that does not contain the isolated polynucleotide.

In a ninth embodiment, the invention concerns a method of obtaining a nucleic acid fragment encoding a substantial portion of a viral movement protein, preferably a plant viral movement protein, comprising the steps of: synthesizing an oligonucleotide primer comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13, 15, 17, 19, 21, 23, 25, 27, 29 and 31 and the complement of such nucleotide sequences; and amplifying a nucleic acid fragment (preferably a cDNA inserted in a cloning vector) using the oligonucleotide primer. The amplified nucleic acid fragment preferably will encode a portion of a viral movement protein amino acid sequence.

In a tenth embodiment, this invention relates to a method of obtaining a nucleic acid fragment encoding all or a substantial portion of the amino acid sequence encoding a viral movement protein comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In an eleventh embodiment, this invention concerns a composition, such as a hybridization mixture, comprising an isolated polynucleotide of the present invention.

In a twelfth embodiment, this invention concerns a method for positive selection of a transformed cell comprising: (a) transforming a host cell with the chimeric gene of the present invention or a construct of the present invention; and (b) growing the transformed host cell, preferably a plant cell, such as a monocot or a dicot, under conditions which allow expression of the viral movement protein polynucleotide in an amount sufficient to complement a null mutant to provide a positive selection means.

BRIEF DESCRIPTION OF THE SEQUENCE LISTINGS

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"). Nucleotide sequences, SEQ ID NOs:1, 3, 5, 7, 9, 11, 13, 15, 17, 19, 21, 23, 25, 27, 29 and 31 and amino acid sequences SEQ ID NOs:2, 4, 6, 8, 10, 12, 14, 16, 18, 20, 22, 24, 26, 28, 30 and 32 were determined by further sequence analysis of cDNA clones encoding the amino acid sequences set forth in SEQ ID NOs:34, 36, 38, 40, 42, 44, 46, 48, 50, 52, 54 and 56. Nucleotide SEQ ID NOs:31, 35, 37, 39, 41, 43, 45, 47, 49, 51, 52, 53 and 55 and amino acid SEQ ID NOs:34, 36, 38, 40, 42, 44, 46, 48, 50, 52, 54 and 56 were among those disclosed in a U.S. Provisional Application No. 60/128,092, filed Apr. 7, 1999.

The sequence descriptions and Sequence Listing attached hereto comply with the rules governing nucleotide and/or amino acid sequence disclosures in patent applications as set forth in 37 C.F.R. §1.821-1.825.

TABLE 1

Viral Movement Proteins

| | | SEQ ID NO: | |
|---|---|---|---|
| Protein | Clone Designation | (Nucleotide) | (Amino Acid) |
| Viral Movement Protein | vpl1c.pk004.d6 | 1 | 2 |
| Viral Movement Protein | cta1n.pk0056.d7 (CGS) | 3 | 4 |
| Viral Movement Protein | cta1n.pk0070.g5 (CGS) | 5 | 6 |
| Viral Movement Protein | Contig (CGS) composed of: ehb2c.pk007.b10 ehb2c.pk008.c17 ehb2c.pk012.h20 ehb2c.pk017.o18 | 7 | 8 |

TABLE 1-continued

Viral Movement Proteins

| | | SEQ ID NO: | |
|---|---|---|---|
| Protein | Clone Designation | (Nucleotide) | (Amino Acid) |
| Viral Movement Protein | wr1.pk151.c12 (CGS) | 9 | 10 |
| Viral Movement Protein | rrl.pk087.f5 (CGS) | 11 | 12 |
| Viral Movement Protein | src3c.pk024.h11 (CGS) | 13 | 14 |
| Viral Movement Protein | p0010.cbpcf32r (CGS) | 15 | 16 |
| Viral Movement Protein | ehb1c.pk001.a20 (EST) | 17 | 18 |
| Viral Movement Protein | sls2c.pk011.d4 (CGS) | 19 | 20 |
| Viral Movement Protein | src2c.pk005.o15 (CGS) | 21 | 22 |
| Viral Movement Protein | wlm96.pk039.k12 (CGS) | 23 | 24 |
| Viral Movement Protein | rsl1n.pk010.i2 (FIS) | 25 | 26 |
| Viral Movement Protein | rdr1f.pk001.g6 (CGS) | 27 | 28 |
| Viral Movement Protein | sls1c.pk023.c9 (CGS) | 29 | 30 |
| Viral Movement Protein | wre1n.pk0035.f6 (CGS) | 31 | 32 |
| Viral Movement Protein | Contig composed of: cta1n.pk0056.d7 (EST) p0058.chpbn09r (EST) | 33 | 34 |
| Viral Movement Protein | cta1n.pk0070.g5 (EST) | 35 | 36 |
| Viral Movement Protein | wr1.pk151.c12 (EST) | 37 | 38 |
| Viral Movement Protein | rrl.pk087.f5 (EST) | 39 | 40 |
| Viral Movement Protein | Contig composed of: src2c.pk015.m1 src3c.pk024.h11 (EST) | 41 | 42 |
| Viral Movement Protein | p0010.cbpcf32r (EST) | 43 | 44 |
| Viral Movement Protein | src2c.pk005.o15 (EST) | 45 | 46 |
| Viral Movement Protein | wlm96.pk039.k12 (EST) | 47 | 48 |
| Viral Movement Protein | rsl1n.pk010.i2 (EST) | 49 | 50 |
| Viral Movement Protein | rdr1f.pk001.g6 (EST) | 51 | 52 |
| Viral Movement Protein | sls1c.pk023.c9 (EST) | 53 | 54 |
| Viral Movement Protein | wre1n.pk0035.f6 (EST) | 55 | 56 |

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 60 contiguous nucleotides, preferably at least 40 contiguous nucleotides, most preferably at least 30 contiguous nucleotides derived from SEQ ID NOs:1, 3, 5, 7, 9, 11, 13, 15, 17, 19, 21, 23, 25, 27, 29 and 31 or the complement of such sequences.

The term "isolated polynucleotide" refers to a polynucleotide that is substantially free from other nucleic acid sequences, such as and not limited to other chromosomal and extrachromosomal DNA and RNA. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13, 15, 17, 19, 21, 23, 25, 27, 29 and 31 and the complement of such nucleotide sequences may be used in methods of selecting an isolated polynucleotide that affects the expression of a viral movement protein in a host cell. A method of selecting an isolated polynucleotide that affects the level of expression of a polypeptide in a virus or in a host cell (eukaryotic, such as plant or yeast, prokaryotic such as bacterial) may comprise the steps of: constructing an isolated polynucleotide of the present invention or a chimeric gene of the present invention; introducing the isolated polynucleotide or the chimeric gene into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403-410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry* of Plants 15:1-82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) Mol. Biotechnol. 3:225-236).

"3' non-coding sequences" refers to nucleotide sequences located downstream of a coding sequence and includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) Plant Cell 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. "Expression" may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Null mutant" refers to a host cell which either lacks the expression of a certain polypeptide or expresses a polypeptide which is inactive or does not have any detectable expected enzymatic function.

"Mature protein" refers to a post-translationally processed polypeptide; i.e., one from which any pre- or propeptides present in the primary translation product have been removed.

"Precursor protein" refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) Ann. Rev. Plant Phys. Plant Mol. Biol. 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) Plant Phys. 100:1627-1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) Meth. Enzymol. 143:277) and particle-accelerated or "gene gun" transformation technology (Klein et al. (1987) Nature (London) 327:70-73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"PCR" or "polymerase chain reaction" is well known by those skilled in the art as a technique used for the amplification of specific DNA segments (U.S. Pat. Nos. 4,683,195 and 4,800,159).

The present invention concerns an isolated polynucleotide comprising a nucleotide sequence selected from the group consisting of: (a) a first nucleotide sequence encoding a polypeptide of at least 129 amino acids having at least 95% identity based on the Clustal method of alignment when compared to a polypeptide selected from the group consisting of SEQ ID NOs:2, 4, 6, 8, 10, 12, 14, 16, 18, 20, 22, 24, 26, 28, 30 and 32 or (b) a second nucleotide sequence comprising the complement of the first nucleotide sequence.

Preferably, the first nucleotide sequence comprises a nucleic acid sequence selected from the group consisting of SEQ ID NOs:1, 3, 5, 7, 9, 11, 13, 15, 17, 19, 21, 23, 25, 27, 29 and 31, that codes for the polypeptide selected from the group consisting of SEQ ID NOs:2, 4, 6, 8, 10, 12, 14, 16, 18, 20, 22, 24, 26, 28, 30 and 32.

Nucleic acid fragments encoding at least a portion of several viral movement proteins have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other viral movement proteins, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequence(s) can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998-9002) to generate cDNAs by using PCR to amply copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673-5677; Loh et al. (1989) *Science* 243:217-220). Products generated by the 3' and 5' RACE procedures can be combined to generate full-length cDNAs (Frohman and Martin (1989) *Techniques* 1:165). Consequently, a polynucleotide comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13, 15, 17, 19, 21, 23, 25, 27, 29 and 31 and the complement of such nucleotide sequences may be used in such methods to obtain a nucleic acid fragment encoding a substantial portion of an amino acid sequence of a polypeptide.

The present invention relates to a method of obtaining a nucleic acid fragment encoding a substantial portion of a viral movement protein, preferably a substantial portion of a plant viral movement protein polypeptide, comprising the steps of: synthesizing an oligonucleotide primer comprising a nucleotide sequence of at least 60 (preferably at least 40, more preferably at least 30) contiguous nucleotides derived from a nucleotide sequence selected from the group consisting of SEQ ID NOs:1, 3, 5, 7, 9, 11, 13, 15, 17, 19, 21, 23, 25, 27, 29 and 31 and the complement of such nucleotide sequences; and amplifying a nucleic acid fragment (preferably a cDNA inserted in a cloning vector) using the oligonucleotide primer. The amplified nucleic acid fragment preferably will encode a portion of a viral movement protein.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1-34; Maniatis).

In another embodiment, this invention concerns viruses and host cells comprising either the chimeric genes of the invention as described herein or an isolated polynucleotide of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of viral movement-like protein activity in those cells.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411-2418; De Almeida et al. (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247-253), signal sequences or sequences encoding endoplasmic reticulum localization (Chrispeels (1991) *Ann. Rev. Plant Phys. Plant Mol. Biol.* 42:21-53), or nuclear localization signals (Raikhel (1992) *Plant Phys.* 100:1627-1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns a polypeptide of at least 129 amino acids that has at least 95% identity based on the Clustal method of alignment when compared to a polypeptide selected from the group consisting of SEQ ID NOs:2, 4, 6, 8, 10, 12, 14, 16, 18, 20, 22, 24, 26, 28, 30 and 32.

The instant polypeptides (or portions thereof) may be produced in heterologous host cells, particularly in the cells of microbial hosts, and can be used to prepare antibodies to the proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded viral movement protein. An example of a vector for high level expression of the instant polypeptides in a bacterial host is provided (Example 6).

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174-181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314-331).

The production and use of plant gene-derived probes for use in genetic mapping is described in Bernatzky and Tanksley (1986) *Plant Mol. Biol. Reporter* 4:37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp 319-346, and references cited therein).

In another embodiment, nucleic acid probes derived from the instant nucleic acid sequences may be used in direct fluorescence in situ hybridization (FISH) mapping (Trask (1991) *Trends Genet.* 7:149-154). Although current methods of FISH mapping favor use of large clones (several to several hundred KB; see Laan et al. (1995) *Genome Res.* 5:13-20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95-96), polymorphism of PCR-amplified fragments (CAPS; Sheffield et al. (1993) *Genomics* 16:325-332), allele-specific ligation (Landegren et al. (1988) *Science* 241:1077-1080), nucleotide extension reactions (Sokolov (1990) *Nucleic Acid Res.* 18:3671), Radiation Hybrid Mapping (Walter et al. (1997) *Nat. Genet.* 7:22-28) and Happy Mapping (Dear and Cook (1989) *Nucleic Acid Res.* 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402-9406; Koes et al. (1995) *Proc. Natl. Acad. Sci USA* 92:8149-8153; Bensen et al. (1995) *Plant Cell* 7:75-84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries; Isolation and Sequencing of cDNA Clones cDNA libraries representing mRNAs from various *Arabidosis*, grape, corn, rubber tre, rice, soybean and wheat tissues were prepared. The characteristics of the libraries are described below.

TABLE 2 cDNA Libraries from *Arabidosis*, Grape, Corn, Rubber Tree, Rice, Soybean and Wheat

| Library | Tissue | Clone |
|---|---|---|
| cta1n | Corn tassel* | cta1n.pk0056.d7 |
| | | cta1n.pk0070.g5 |
| ehb1c | Para rubber tree fast bleeding latex tapped in 2nd day of 3 day tapping cycle | ehb1c.pk001.a20 |
| | Para rubber tree latex tapped in 2nd day of 3 day tapping cycle | ehb2c.pk007.b10 |
| | | ehb2c.pk008.c17 |
| | | ehb2c.pk012.h20 |
| | | ehb2c.pk017.o18 |
| p0010 | Corn log phase suspension cells treated with A23187 to induce mass apoptosis** | p0010.cbpcf32r |
| rdr1f | Rice developing root of 10 day old plant | rdr1f.pk001.g6 |
| rr1 | Rice root of two week old developing seedling | rr1.pk087.f5 |
| rsl1n | Rice 15 day old seedling* | rsl1n.pk010.i2 |
| sls1c | Soybean Infected With *Sclerotiorum* Mycelium | sls1c.pk023.c9 |
| sls2c | Soybean Infected With *Sclerotiorum* Mycelium | sls2c.pk011.d4 |
| src2c | Soybean 8 Day Old Root Infected With Cyst Nematode *Heterodera glycenis* | src2c.pk005.o15 |
| src3c | Soybean 8 Day Old Root Infected With Cyst Nematode *Heterodera glycenis* | src3c.pk024.h11 |
| wlm96 | Wheat seedlings 96 hours after inoculation with *Erysiphe graminis f.* sp *tritici* | wlm96.pk039.k12 |

TABLE 2-continued cDNA Libraries from *Arabidosis*, Grape, Corn,
Rubber Tree, Rice, Soybean and Wheat

| Library | Tissue | Clone |
|---|---|---|
| wr1 | Wheat root from 7 day old seedling | wr1.pk151.c12 |
| wre1n | Wheat root from 7 day old etiolated seedling* | wre1n.pk0035.f6 |
| vpl1c | Grape in vitro plantlets | vpl1c.pk004.d6 |

*These libraries were normalized essentially as described in U.S. Pat. No. 5,482,845, incorporated herein by reference.
**A23187 is commercially available from Calbiochem-Noavbiochem Corp.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651-1656). The resulting ESTs are analyzed using a Perkin Elmer Model 377 fluorescent sequencer.

Example 2

Identification of cDNA Clones cDNA clones encoding viral movement proteins were identified by conducting BLAST (Basic Local Alignment Search Tool; Altschul et al. (1993) *J. Mol. Biol.* 215:403-410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EBML, and DDBJ databases). The cDN sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266-272) provided by the NCBI. For convenience, the P-value (probability) of observing a match of a cDNA sequence to a sequence contained in the searched databases merely by chance as calculated by BLAST are reported herein has "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Viral Movement Proteins

The BLASTX search using the EST sequences from clones listed in Table 3 revealed similarity of the polypeptides encoded by the cDNAs to viral movement proteins from *Oryza sativa* (NCBI Identifier No. gi 3603473), *Arabidopsis thaliana* (NCBI Identifier No. gi 2911047), *Oryza sativa* (NCBI Identifier No. gi 2920839), *Arabidopsis thaliana* (NCBI Identifier No. gi 2911073), *Cicer arietinum* (NCBI Identifier No. gi 3860331) and *Zea mays* (NCBI Identifier No. gi 1498055). Shown in Table 3 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 3

BLAST Results for Sequences Encoding Polypeptides Homologous to
*Oryza sativa*, *Zea mays*, *Cicer arietinum* and
*Arabidopsis thaliana* Viral Movement Proteins

| Clone | Status | BLAST pLog Score |
|---|---|---|
| vpl1c.pk004.d6 | EST | 52.52 (gi 3603473) |
| cta1n.pk0056.d7 | CGS | 57.10 (gi 3603473) |
| cta1n.pk0070.g5 | CGS | 62.22 (gi 3603473) |
| Contig composed of: ehb2c.pk007.b10 ehb2c.pk008.c17 ehb2c.pk012.h20 ehb2c.pk017.o18 | CGS | 46.00 (gi 3603473) |
| wr1.pk151.c12 | CGS | 66.00 (gi 3603473) |
| rr1.pk087.f5 | CGS | 33.52 (gi 2911047) |
| src3c.pk024.h11 | CGS | 39.40 (gi 2911047) |
| p0010.cbpcf32r | CGS | 61.10 (gi 2920839) |
| ehb1c.pk001.a20 | EST | 30.10 (gi 2920839) |
| sls2c.pk011.d4 | CGS | 34.05 (gi 2920839) |
| src2c.pk005.o15 | CGS | 31.30 (gi 2920839) |
| wlm96.pk039.k12 | CGS | 61.40 (gi 2920839) |
| rsl1n.pk010.i2 | FIS | 66.70 (gi 2911073) |
| rdr1f.pk001.g6 | CGS | 61.00 (gi 1498055) |
| sls1c.pk023.c9 | CGS | 58.30 (gi 3860331) |
| wre1n.pk0035.f6 | CGS | 45.00 (gi 1498055) |

The data in Table 4 represents a calculation of the percent identity of the amino acid sequences set forth in SEQ ID NOs:2, 4, 6, 8, 10, 12, 14, 16, 18, 20, 22, 24, 26, 28, 30 and 32 and the *Oryza sativa*, *Zea mays*, *Cicer arietinum* and *Arabidopsis thaliana* sequences.

TABLE 4

Percent Identity of Amino Acid Sequences Deduced From the Nucleotide
Sequences of cDNA Clones Encoding Polypeptides Homologous to
*Oryza sativa*, *Zea mays*, *Cicer arietinum* and
*Arabidopsis thaliana*

| SEQ ID NO. | Percent Identity to |
|---|---|
| 2 | 83% (gi 3603473) |
| 4 | 89% (gi 3603473) |
| 6 | 90% (gi 3603473) |
| 8 | 82% (gi 3603473) |

TABLE 4-continued

Percent Identity of Amino Acid Sequences Deduced From the Nucleotide Sequences of cDNA Clones Encoding Polypeptides Homologous to *Oryza sativa*, *Zea mays*, *Cicer arietinum* and *Arabidopsis thaliana*

| SEQ ID NO. | Percent Identity to |
|---|---|
| 10 | 92% (gi 3603473) |
| 12 | 45% (gi 2911047) |
| 14 | 48% (gi 2911047) |
| 16 | 84% (gi 2920839) |
| 18 | 73% (gi 2920839) |
| 20 | 71% (gi 2920839) |
| 22 | 70% (gi 2920839) |
| 24 | 74% (gi 2920839) |
| 26 | 36% (gi 2911073) |
| 28 | 91% (gi 1498055) |
| 30 | 88% (gi 3860331) |
| 32 | 71% (gi 1498055) |

Sequence alignments and percent identity calculations were performed using the Megalign program of the LASERGENE bioinformatics computing suite (DNASTAR Inc., Madison, Wis.) Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE 1, GAP PENALTY=3, WINDOW W=5 and DIAGONALS SAVED=5. Sequence alignments, BLAST scores and probabilities indicate that the nucleic acid fragments comprising the instant cDNA clones encode a substantial portion of a viral movement protein.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810-812) and the 3' region of the nopaline synthase gene from the T-DNA of the Ti plasmid of *Agrobacterium tumefaciens*.

The particle bombardment method (Klein et al. (1987) *Nature* 327:70-73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5-cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate.

After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833-839).

Example 5

Expression of Chimeric Genes in Dicot Cells

A seed-specific construct composed of the promoter and transcription terminator from the gene encoding the β subunit of the seed storage protein phaseolin from the bean *Phaseolus vulgaris* (Doyle et al. (1986) *J. Biol. Chem.* 261:9228-9238) can be used for expression of the instant polypeptides in transformed soybean. The phaseolin construct includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire construct is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed construct.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810-812), the hygromycin phosphotransferase gene from plasmid pJR225 (from *E. coli*; Gritz et al.(1983) *Gene* 25:179-188) and the 3' region of the nopaline synthase gene from the T-DNA of the Ti plasmid of *Agrobacterium tumefaciens*. The seed construct comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μL spermidine (0.1 M), and 50 μL $CaCl_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125-135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pE-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/mL ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21 (DE3) (Studier et al. (1986) *J. Mol. Biol.* 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

What is claimed is:

1. An isolated polynucleotide comprising:
   (a) a nucleotide sequence encoding a viral movement polypeptide, wherein the amino acid sequence of the polypeptide has at least 90% sequence identity, based on the Clustal method of alignment with multiple alignment default parameters of GAP PENALTY=10 and GAP LENGTH PENALTY=10, and pairwise alignment default parameters of KTUPLE=1, GAP PENALTY=3, WINDOW=5 and DIAGONALS SAVED=5, when compared to SEQ ID NO:4, or
   (b) a complement of the nucleotide sequence, wherein the complement and the nucleotide sequence consist of the same number of nucleotides and are 100% complementary to the nucleotide sequence.

2. The polynucleotide of claim 1, wherein the amino acid sequence of the polypeptide has at least 95% sequence identity, based on the Clustal method of alignment with the default parameters, when compared to SEQ ID NO:4.

3. The polynucleotide of claim 1, wherein the amino acid sequence of the polypeptide comprises SEQ ID NO:4.

4. The polynucleotide of claim 1, wherein the nucleotide sequence comprises SEQ ID NO:3.

5. A vector comprising the polynucleotide of claim 1.

6. A recombinant DNA construct comprising the polynucleotide of claim 1 operably linked to at least one regulatory sequence.

7. A method for transforming a cell, comprising transforming a cell with the polynucleotide of claim 1.

8. A cell comprising the recombinant DNA construct of claim 6.

9. A method for producing a plant comprising transforming a plant cell with the polynucleotide of claim 1 and regenerating a plant from the transformed plant cell.

10. A plant comprising the recombinant DNA construct of claim 9.

11. A seed comprising the recombinant DNA construct of claim 9.

12. A method of altering the level of expression of a viral movement protein in a host cell comprising:
    (a) transforming a host cell with the recombinant DNA construct of claim 6; and
    (b) growing the transformed host cell under conditions that are suitable for expression of the recombinant DNA construct wherein expression of the recombinant DNA construct results in production of altered levels of the viral movement protein in the transformed host cell.

* * * * *

SEQUENCE LISTING

```
<160> NUMBER OF SEQ ID NOS: 56

<210> SEQ ID NO 1
<211> LENGTH: 450
<212> TYPE: DNA
<213> ORGANISM: Vitis sp.
<220> FEATURE:
<221> NAME/KEY: unsure
<222> LOCATION: (445)
<223> OTHER INFORMATION: n = A, C, G or T

<400> SEQUENCE: 1
gggagaaaag gttagaattt tggtttgcat ttggaatctg ttgcaattct caatcagaaa      60
atgcctcaag gaacacttga agtccttctt gtcagtgcca agggtctcga gaacactgat     120
tttctctgta acatggatcc ttatgttgtt ctcacttgcc gcactcagga gcagaaaagc     180
agtgttgcat caggaaaagg gtctgaccca gaatggaatg aacattttgt attcaccata     240
tctgaaggca tctcagaact caccattaaa ataatggaca gtgatagcgg tagtggtgat     300
gattttgtgg gagaagcaac cattccacta gaggcactct tcacggaagg aagcctggag     360
ccaagcaccg gtacaatgtt gttaaagacc aaggaatatt gtggagagat taaagttggc     420
ctcactttca ctcaaaaggg aaaangtgat                                       450

<210> SEQ ID NO 2
<211> LENGTH: 130
<212> TYPE: PRT
<213> ORGANISM: Vitis sp.
<220> FEATURE:
<221> NAME/KEY: UNSURE
<222> LOCATION: (129)
<223> OTHER INFORMATION: Xaa = any amino acid

<400> SEQUENCE: 2

Met Pro Gln Gly Thr Leu Glu Val Leu Leu Val Ser Ala Lys Gly Leu
 1               5                  10                  15

Glu Asn Thr Asp Phe Leu Cys Asn Met Asp Pro Tyr Val Val Leu Thr
            20                  25                  30

Cys Arg Thr Gln Glu Gln Lys Ser Ser Val Ala Ser Gly Lys Gly Ser
        35                  40                  45

Asp Pro Glu Trp Asn Glu His Phe Val Phe Thr Ile Ser Glu Gly Ile
    50                  55                  60

Ser Glu Leu Thr Ile Lys Ile Met Asp Ser Asp Ser Gly Ser Gly Asp
```

```
                65                  70                  75                  80
Asp Phe Val Gly Glu Ala Thr Ile Pro Leu Glu Ala Leu Phe Thr Glu
                    85                  90                  95
Gly Ser Leu Glu Pro Ser Thr Gly Thr Met Leu Leu Lys Thr Lys Glu
                100                 105                 110
Tyr Cys Gly Glu Ile Lys Val Gly Leu Thr Phe Thr Gln Lys Gly Lys
            115                 120                 125
Xaa Asp
    130

<210> SEQ ID NO 3
<211> LENGTH: 916
<212> TYPE: DNA
<213> ORGANISM: Zea mays

<400> SEQUENCE: 3
gcacgagcac gccgcctcca tgtgggtggg gaggcaaacg cgttcgtcca tctctgaaac    60
tcaaacgcct tgtattggag catactacag gagtacttct gtacaaatat aaataccccct  120
ggcgagttgg gttgggtcta tctcgcaatc gaggcgtttt tttctgctt cgtaagttcg    180
tggtcgatcc agcgagcgag cgagcagacc ggcggctaac cgcggaggga gagatggcgc    240
aggggacgct ggaggtgctt ctcgtcggag ccaggggcct cgagaacacc gattacctga    300
gcaacatgga ccctacgcg cttctgcaat gtcgctccca cgagcagaag agcagcgtcg     360
catctggcaa aggctgtgaa cctgagtgga acgagacctt cgtgttcacc gtctccgatg    420
gcgcagcaga gctgttcatc aagctcctgg acagtgacgg tggcactgat gacgattttg    480
ttggtgaggc aacgattcct ctggaagcag tttacacgga aggaaacatc cctccgactg    540
tttacaatgt tgtgaaagac gaagaatacc gcggagaaat caaagttggc ctcacgttca    600
ctccagagga ccagggcttc tgaggaataa cttggcgtgt ggccgctgga actggaggca    660
gcaggcagtc gtcttatgat tcagaagcaa acgacggatc gattcccttg atgtactgca    720
gtccagtgag cgtgcatcta aacttgtag aagaagcctg caacatgatc acgggatcct     780
gtactgcatc actctaaagc ctagctaaaa ccaccagctc ctgtacttga tgccgggcgg    840
gcttgtcatg tactgaaacc tacaataacg gtcgccgaac cccactcttt gatgttaaaa    900
aaaaaaaaaa aaaaaa                                                    916

<210> SEQ ID NO 4
<211> LENGTH: 129
<212> TYPE: PRT
<213> ORGANISM: Zea mays

<400> SEQUENCE: 4

Met Ala Gln Gly Thr Leu Glu Val Leu Leu Val Gly Ala Arg Gly Leu
1               5                   10                  15
Glu Asn Thr Asp Tyr Leu Ser Asn Met Asp Pro Tyr Ala Leu Leu Gln
            20                  25                  30
Cys Arg Ser His Glu Gln Lys Ser Ser Val Ala Ser Gly Lys Gly Cys
        35                  40                  45
Glu Pro Glu Trp Asn Glu Thr Phe Val Phe Thr Val Ser Asp Gly Ala
    50                  55                  60
Ala Glu Leu Phe Ile Lys Leu Leu Asp Ser Asp Gly Gly Thr Asp Asp
65                  70                  75                  80
Asp Phe Val Gly Glu Ala Thr Ile Pro Leu Glu Ala Val Tyr Thr Glu
                85                  90                  95
```

```
Gly Asn Ile Pro Pro Thr Val Tyr Asn Val Val Lys Asp Glu Glu Tyr
            100                 105                 110

Arg Gly Glu Ile Lys Val Gly Leu Thr Phe Thr Pro Glu Asp Gln Gly
        115                 120                 125
Phe

<210> SEQ ID NO 5
<211> LENGTH: 876
<212> TYPE: DNA
<213> ORGANISM: Zea mays

<400> SEQUENCE: 5
gcacgaggtt cgttcacgcc acaggcaagg cacagggggct tgtgagggag agcgaggagc      60
ggaggaggac atggtgcacg ggacgctgga agtgctgctc gttggggcca agggcctcga     120
gaacaccgat tacctctgta acatggatcc gtatgcaatt ctcaagtgcc gttcacagga     180
gcagaagagc agtattgcaa ctggaaaagg aactacccct gagtggaatg aaaactttat     240
cttcactgtg tctgaccgga acagacttt ggtaatcaag cttatggaca gtgatacagg     300
cacagcagat gactttgttg gtgaagcaac gattccattg gaagcagtgt atactgaaag     360
gagcattcca ccaacactct ataatgttgt gaaaggtgaa aaatactgcg gggaaatcaa     420
agttggtctc acattcactc ctgaggatac tcgccagcgg ggtctcccag gacttcgg     480
tggatggaag caatcatctt agagctagat gctttaaggg tgcaccagag cacagcgaca     540
attcatgcgc ttggagcctt cagccgtcga gtacttcatg ctaatgcaga attcattcga     600
tttggcttct tttgattgtt tcagaagaag tgttattagt gagtttcaac aaaaaatagc     660
tccatattgc tctatatccc gtattggaaa ttctaaggcc gtttgtgatt actgcttaca     720
acaagaagtt tgcttctag ttcccactac gcttttttt gaagttttga gtggaacatc     780
tttgtgttca acgtttgggg aggtgtaggc cagtaatact gcaagaaagg aataatttcc     840
cttgcagcaa cattgttttt tgtgatcctt gaaaaa                                876

<210> SEQ ID NO 6
<211> LENGTH: 143
<212> TYPE: PRT
<213> ORGANISM: Zea mays

<400> SEQUENCE: 6

Met Val His Gly Thr Leu Glu Val Leu Leu Val Gly Ala Lys Gly Leu
  1               5                  10                  15

Glu Asn Thr Asp Tyr Leu Cys Asn Met Asp Pro Tyr Ala Ile Leu Lys
             20                  25                  30

Cys Arg Ser Gln Glu Gln Lys Ser Ser Ile Ala Thr Gly Lys Gly Thr
         35                  40                  45

Thr Pro Glu Trp Asn Glu Asn Phe Ile Phe Thr Val Ser Asp Arg Thr
     50                  55                  60

Thr Asp Leu Val Ile Lys Leu Met Asp Ser Asp Thr Gly Thr Ala Asp
 65                  70                  75                  80

Asp Phe Val Gly Glu Ala Thr Ile Pro Leu Glu Ala Val Tyr Thr Glu
                 85                  90                  95

Arg Ser Ile Pro Pro Thr Leu Tyr Asn Val Val Lys Gly Glu Lys Tyr
            100                 105                 110

Cys Gly Glu Ile Lys Val Gly Leu Thr Phe Thr Pro Glu Asp Thr Arg
        115                 120                 125

Gln Arg Gly Leu Pro Glu Asp Phe Gly Gly Trp Lys Gln Ser Ser
```

```
<210> SEQ ID NO 7
<211> LENGTH: 771
<212> TYPE: DNA
<213> ORGANISM: Hevea brasiliensis
<220> FEATURE:
<221> NAME/KEY: unsure
<222> LOCATION: (671)
<223> OTHER INFORMATION: n = A, C, G or T
<220> FEATURE:
<221> NAME/KEY: unsure
<222> LOCATION: (721)
<223> OTHER INFORMATION: n = A, C, G or T
<220> FEATURE:
<221> NAME/KEY: unsure
<222> LOCATION: (752)
<223> OTHER INFORMATION: n = A, C, G or T
<220> FEATURE:
<221> NAME/KEY: unsure
<222> LOCATION: (767)
<223> OTHER INFORMATION: n = A, C, G or T
<220> FEATURE:
<221> NAME/KEY: unsure
<222> LOCATION: (769)
<223> OTHER INFORMATION: n = A, C, G or T

<400> SEQUENCE: 7
cttaattttt aaaaacatta ttagccttcc tcgttaatca ttcactctcc ctataagatg      60
cacagatacc caagggcag agatccaaga actcatttca atctaaattc ctgttgagtt     120
ttaagtcttt tcttttcgc ttttttggatt caattctggt ccaaaaatgc ctctaggaac    180
tgttgaagtc ctacttgttg gtgctaaggg tcttgaaaac actgattttc tcaatggcgt    240
ggacccttat gtcgtcctcg cttgccgtac ccaggagcag aaaagcagtg ttgcttcagg    300
gaaagggagt gaaccagaat ggaatgagaa attctcattt gaggtatcag atggtgacac    360
agaactcaca ttgaaaatca tggacagtga tgttggtgct gcagatgatt ttgttggaga    420
agcaaccatt cccttgagc cattgttttt ggaaggaaac ctcccatcta cggcgtacaa     480
agttgtcaaa gaacaagaat acaagggaga gattacagtg ggcctcacct tcaccccaga    540
ggtagagatg gacaacgtcg gagtggatgg atacgatttt cggttataat attaactagc    600
atcttggtgt ggaaatggca aggactgctt ttggtttgga gatggcaaaa gagactccgt    660
ttttaacgtc natgttgttg ttgaaaactt ggttttgat gtttgcaaaa aatacccgat     720
nttgttttaa agaaaccctt tttgggggt tngaaattga atttggnant t              771

<210> SEQ ID NO 8
<211> LENGTH: 140
<212> TYPE: PRT
<213> ORGANISM: Hevea brasiliensis

<400> SEQUENCE: 8

Met Pro Leu Gly Thr Val Glu Val Leu Leu Val Gly Ala Lys Gly Leu
 1               5                  10                  15

Glu Asn Thr Asp Phe Leu Asn Gly Val Asp Pro Tyr Val Val Leu Ala
            20                  25                  30

Cys Arg Thr Gln Glu Gln Lys Ser Ser Val Ala Ser Gly Lys Gly Ser
        35                  40                  45

Glu Pro Glu Trp Asn Glu Lys Phe Ser Phe Glu Val Ser Asp Gly Asp
    50                  55                  60

Thr Glu Leu Thr Leu Lys Ile Met Asp Ser Asp Val Gly Ala Ala Asp
65                  70                  75                  80
```

```
Asp Phe Val Gly Glu Ala Thr Ile Pro Leu Glu Pro Leu Phe Leu Glu
                85                  90                  95

Gly Asn Leu Pro Ser Thr Ala Tyr Lys Val Val Lys Glu Gln Glu Tyr
            100                 105                 110

Lys Gly Glu Ile Thr Val Gly Leu Thr Phe Thr Pro Glu Val Glu Met
        115                 120                 125

Asp Asn Val Gly Val Asp Gly Tyr Asp Phe Arg Leu
    130                 135                 140
```

<210> SEQ ID NO 9
<211> LENGTH: 874
<212> TYPE: DNA
<213> ORGANISM: Triticum aestivum

<400> SEQUENCE: 9

```
gcacgaggcc gagctttcca tttttcaact cctagtccta tacatacagc ggaaccccgg      60
ggctcggatc ggatctacag caattagtct cgaccttcag tcgtgccgcc tgctcatcag     120
catataattc ctgatcgagc gagcgggaga ggaaggcgag atcaggccgg agagaagat     180
ggcgcagggg acgctggagg tgctgctcgt gggagccaag ggcctcgaga acaccgacta     240
cctctgcaac atggacccgt acgcggttct aaaatgcacc tcgcaggagc aaaagagcac     300
cgtcgcctct ggaaagggaa gtgatcctga gtggaacgaa acctttgtgt tcaccgtctc     360
tgagaatgca actgagcttg tcatcaagct actggacagt gatggtggca ggacgacga     420
cagcgttggt gaagcaacga tcccattgga tggagtgtac actgaaggaa gcatcccacc     480
aactgtttac aatgttgtca agacgaaga gtaccgtgga gaaatcaaaa ttggtctgac     540
gttcactccg gaggaggctc gtgatcagga tcaacccgag gaaaactatg gtgggtggaa     600
ccaatcatct tgagaagaag caggtgcttt gctgaactat ggtgcgtgac aagtcgtgtg     660
ctagaactaa agcctatttt aattgttaaa gactgtattt gtcgttgatt ccctcaatta     720
tggataagct acgaatctac ttattgattg gtatcgtttt ctaatattca aatttgtaat     780
aacagtgttc cccacttgta tgaagtatga gcctctttaa tgtcactaaa ctgagttgca     840
aaaaaaaaaa aaaaaaaaaa aaaaaaaaaa aaaa                                  874
```

<210> SEQ ID NO 10
<211> LENGTH: 144
<212> TYPE: PRT
<213> ORGANISM: Triticum aestivum

<400> SEQUENCE: 10

```
Met Ala Gln Gly Thr Leu Glu Val Leu Leu Val Gly Ala Lys Gly Leu
  1               5                  10                  15

Glu Asn Thr Asp Tyr Leu Cys Asn Met Asp Pro Tyr Ala Val Leu Lys
                 20                  25                  30

Cys Thr Ser Gln Glu Gln Lys Ser Thr Val Ala Ser Gly Lys Gly Ser
             35                  40                  45

Asp Pro Glu Trp Asn Glu Thr Phe Val Phe Thr Val Ser Glu Asn Ala
        50                  55                  60

Thr Glu Leu Val Ile Lys Leu Leu Asp Ser Asp Gly Gly Thr Asp Asp
 65                  70                  75                  80

Asp Ser Val Gly Glu Ala Thr Ile Pro Leu Asp Gly Val Tyr Thr Glu
                 85                  90                  95

Gly Ser Ile Pro Pro Thr Val Tyr Asn Val Val Lys Asp Glu Glu Tyr
            100                 105                 110
```

Arg Gly Glu Ile Lys Ile Gly Leu Thr Phe Thr Pro Glu Glu Ala Arg
            115                 120                 125

Asp Gln Asp Gln Pro Glu Glu Asn Tyr Gly Gly Trp Asn Gln Ser Ser
    130                 135                 140

<210> SEQ ID NO 11
<211> LENGTH: 1482
<212> TYPE: DNA
<213> ORGANISM: Oryza sativa

<400> SEQUENCE: 11

```
gcacgagatc gtcaactcag ctcctctctt tcttcccctc ccccgctcct ccgcgagacg      60
acccgcgccc gtagccatcc atgtcgatac aaggccagat cctcgaagtc agagtcactg     120
ggtgcaggaa gctgagggac acggagttct tcacgcggca ggatccctac gtctgcatcg     180
agtatgccac caacaagttc cgcacccgca cctgcaccga tgggggaagg aaccctactt     240
ttgacgagaa gtttcatata cctctcattg aggggcttcg tgagctaacc gtcacagtgt     300
ggaacagcaa cacgctcacc catgatgatt tcattggcaa tggcagggtg cagctgcata     360
aggtgcttac gcgtggctat gatgatgcct catggcccct ccagacacgc catatgaggt     420
ctgctgggga agtgacgctc attatgcatt ttgatgtttc agcaatgaag aacaagccgg     480
gaaaaatttc tgccgcgtca accacacatt ctgttcttcc agtgccggta ccagcagtac     540
catatgctgc ccctcacct tcatacgcac tacccctgc aggatacct gcagtaccgc      600
catatcaatc ctatcctgct agccatgtcc ggcgccata tcctacttca gcataccca     660
atccaccacc atctctgcta gctcgcgatg ttgagcatgc ggcataccct cctacaagta     720
caacatatcc tccacagccg tacccaccac agccgcaggg acaaacatac ccaccgcagc     780
cgcagggaga aacataccaa ccgcagccgc agcgagaaac atacccaccg cagcctcaag     840
tacaaccata cccaccaaag ccacagggac aaccataccc accgcagccg cagggacaac     900
catatccacc gcaaccatat ggacaaactt acccaccacc tccaaaagga cagcccacat     960
atccacctgc gccctatcct tcaacttatc caccagcacc atattgatat ggcacacttg    1020
gtggactgaa gttgtccaca tacaaaagca agtaagcaac aagtgatgat cagttcttat    1080
atttatccag ggtatccagc cttcatcatc cagttaattg aaacaaatga atcattcct     1140
gaagcgattc atgtcaacat cttagcaacc aatggtagta gttaccatct ggtatgtatc    1200
atatatcata gcttgcagaa tgtcacgaat ggaatttgtt cgattatgtt gtatgttttg    1260
ggcttgttgt aacagtgatc caccttgtt ctgttttgag gtcatgtttg gctgttctgt    1320
gactgtaact actgctttt acaaggggg gaagcagtaa ttctagttct acctgcaact    1380
gcctgataag tgttaactgt gaaaagttgc agtagcttgt cgactttgta ccatgttgtt    1440
tgagatgctc aataaatttg ctttgtacta aaaaaaaaa aa                        1482
```

<210> SEQ ID NO 12
<211> LENGTH: 308
<212> TYPE: PRT
<213> ORGANISM: Oryza sativa

<400> SEQUENCE: 12

Met Ser Ile Gln Gly Gln Ile Leu Glu Val Arg Val Thr Gly Cys Arg
  1               5                  10                  15

Lys Leu Arg Asp Thr Glu Phe Phe Thr Arg Gln Asp Pro Tyr Val Cys
             20                  25                  30

Ile Glu Tyr Ala Thr Asn Lys Phe Arg Thr Arg Thr Cys Thr Asp Gly

```
                35                  40                  45
Gly Arg Asn Pro Thr Phe Asp Glu Lys Phe His Ile Pro Leu Ile Glu
 50                  55                  60
Gly Leu Arg Glu Leu Thr Val Thr Val Trp Asn Ser Asn Thr Leu Thr
 65                  70                  75                  80
His Asp Asp Phe Ile Gly Asn Gly Arg Val Gln Leu His Lys Val Leu
                 85                  90                  95
Thr Arg Gly Tyr Asp Asp Ala Ser Trp Pro Leu Gln Thr Arg His Met
                100                 105                 110
Arg Ser Ala Gly Glu Val Thr Leu Ile Met His Phe Asp Val Ser Ala
            115                 120                 125
Met Lys Asn Lys Pro Gly Lys Ile Ser Ala Ala Ser Thr Thr His Ser
130                 135                 140
Val Leu Pro Val Pro Val Pro Ala Val Pro Tyr Ala Ala Pro Ser Pro
145                 150                 155                 160
Ser Tyr Ala Leu Pro Pro Ala Gly Tyr Pro Ala Val Pro Pro Tyr Gln
                165                 170                 175
Ser Tyr Pro Ala Ser His Val Pro Ala Pro Tyr Pro Thr Ser Ala Tyr
            180                 185                 190
Pro His Pro Pro Pro Ser Leu Leu Ala Arg Asp Val Glu His Ala Ala
        195                 200                 205
Tyr Pro Pro Thr Ser Thr Thr Tyr Pro Pro Gln Pro Tyr Pro Pro Gln
210                 215                 220
Pro Gln Gly Gln Thr Tyr Pro Pro Gln Pro Gln Gly Glu Thr Tyr Gln
225                 230                 235                 240
Pro Gln Pro Gln Arg Glu Thr Tyr Pro Pro Gln Pro Gln Val Gln Pro
                245                 250                 255
Tyr Pro Pro Lys Pro Gln Gly Gln Pro Tyr Pro Pro Gln Pro Gln Gly
            260                 265                 270
Gln Pro Tyr Pro Pro Gln Pro Tyr Gly Gln Thr Tyr Pro Pro Pro
        275                 280                 285
Lys Gly Gln Pro Thr Tyr Pro Pro Ala Pro Tyr Pro Ser Thr Tyr Pro
290                 295                 300
Pro Ala Pro Tyr
305

<210> SEQ ID NO 13
<211> LENGTH: 1172
<212> TYPE: DNA
<213> ORGANISM: Glycine max

<400> SEQUENCE: 13
ggtgaattgc aatttcaatt aattagaatt caacgtttgc aaattgcata ttgttcttct      60
cttcctctct tcctctgact ccatgtcgtc gataacgggc atccaggggc aacctcttga     120
ggttacggtg gtttcgtgct ccaagttgaa ggacacagaa tggatttcaa gacaagatcc     180
gtacgttgt gttgagtatg cagcacaaa gttccgaacc agaacctgca cagacggcgg       240
aaaaaacccg gtattccaag agaagttcat ctttccccctc attgaaggcc ttcgggagct    300
caatgtcctt gtttggaaca gcaatactct caccttcgac gatttttatag gaagcggaaa   360
gattcaattg cacaaggttc tctctcaagg cttcgatgac tctgcttggc cacttcagac    420
caaaactggc agatacgctg gtgaagtaaa agtcatattg cattacgcaa ttgcaaatca    480
aaggcataaa ttagtgtcag gccatgctcc atcagcacct ccgtatgtgg caacagcaac    540
```

-continued

```
tcctcccgtc ccttcttcat attctacttc atacccgcca cctccttctg ctacttccta    600
cccaccacca ccatcacctc cctctgcaac tccttaccat acaactggat cttattctta    660
cccaccgccg ccgccacctc ctacagctta ccctccctat tcctcacatt catctcccta    720
tccaccatca tcatacccccc cacagccctc ctcgtatcct cctcctcctc cccatcatc    780 atatccccct gcttcagctt atccatatcc accacctgca ggctatcctt ctggaatata    840
ccctccacca ccttactgac tgagatcttc taccttctca accaaggaac caacatcaac    900
atgccttgta tgccaaaagg gccttcagac tcccttttcaa tgcttgttca aacgccccgt    960
gctttgacct tttgaggtgt cttgcttgta aagtgttat tttatacaca ttcagatcca   1020
attaaagggc accatttttt ttttcgcaat tggatgttca ctgaccattt tccggttttc   1080
ttttgtctcc gtaaggatga aatatctatg aatcgtttat caggttgctc aaaaaaaaaa   1140 aaaaaaaac aaaaaaaaaa aaaaaaaaaa aa                                  1172
```

<210> SEQ ID NO 14
<211> LENGTH: 258
<212> TYPE: PRT
<213> ORGANISM: Glycine max

<400> SEQUENCE: 14

```
Met Ser Ser Ile Thr Gly Ile Gln Gly Gln Pro Leu Glu Val Thr Val
  1               5                  10                  15

Val Ser Cys Ser Lys Leu Lys Asp Thr Glu Trp Ile Ser Arg Gln Asp
             20                  25                  30

Pro Tyr Val Cys Val Glu Tyr Gly Ser Thr Lys Phe Arg Thr Arg Thr
         35                  40                  45

Cys Thr Asp Gly Gly Lys Asn Pro Val Phe Gln Glu Lys Phe Ile Phe
     50                  55                  60

Pro Leu Ile Glu Gly Leu Arg Glu Leu Asn Val Leu Trp Asn Ser
 65                  70                  75                  80

Asn Thr Leu Thr Phe Asp Asp Phe Ile Gly Ser Gly Lys Ile Gln Leu
                 85                  90                  95

His Lys Val Leu Ser Gln Gly Phe Asp Asp Ser Ala Trp Pro Leu Gln
            100                 105                 110

Thr Lys Thr Gly Arg Tyr Ala Gly Glu Val Lys Val Ile Leu His Tyr
        115                 120                 125

Ala Ile Ala Asn Gln Arg His Lys Leu Val Ser Gly His Ala Pro Ser
    130                 135                 140

Ala Pro Pro Tyr Val Ala Thr Ala Thr Pro Pro Val Pro Ser Ser Tyr
145                 150                 155                 160

Ser Thr Ser Tyr Pro Pro Pro Ser Ala Thr Ser Tyr Pro Pro Pro
                165                 170                 175

Pro Ser Pro Pro Ser Ala Thr Pro Tyr His Thr Thr Gly Ser Tyr Ser
            180                 185                 190

Tyr Pro Pro Pro Pro Pro Pro Thr Ala Tyr Pro Pro Tyr Ser Ser
        195                 200                 205

His Ser Ser Pro Tyr Pro Ser Ser Tyr Pro Gln Pro Ser Ser
    210                 215                 220

Tyr Pro Pro Pro Pro Pro Ser Ser Tyr Pro Ala Ser Ala Tyr
225                 230                 235                 240

Pro Tyr Pro Pro Ala Gly Tyr Pro Ser Gly Ile Tyr Pro Pro
                245                 250                 255

Pro Tyr
```

<210> SEQ ID NO 15
<211> LENGTH: 757
<212> TYPE: DNA
<213> ORGANISM: Zea mays

<400> SEQUENCE: 15

| | | | | | |
|---|---|---|---|---|---|
| acccacgcgt | ccgcccacgc | gtccgccgcg | ccgccgcaag | agaggagaga | gcgcctccaa | 60 |
| cgccacctgg | aggagaggac | agcgcgccag | ggaggggag | gaggaagaag | aacatgggga | 120 |
| agggcgtcct | gaaggtgcac | ctcgtcgacg | ccaaggggct | ctccggcaac | gatttcttag | 180 |
| ggaagctgga | cccctacgtg | atcatgcagt | accggagcca | ggagcgcaag | agcagcgtcg | 240 |
| cccgagacca | aggaaggaac | ccgtgctgga | acgaggtgtt | caagttccag | atcaactcgg | 300 |
| ccgcggccaa | cgtgcagcac | aagctcatcc | tccggatcat | ggaccacgac | aacttctcca | 360 |
| gcgacgactt | cctcggcgag | gcgacgatcg | acgtgacgga | catcgtcagc | ctgggcgccg | 420 |
| agcgcggcac | gtaccacctc | aacgcggcca | agcacaacgt | ggtcctcgcc | gacaagacgt | 480 |
| accacggcga | gatcaaggtc | gccatcacct | tcacctccac | ccagacccag | gttcaggaag | 540 |
| atggaggagc | aattggagga | tggaggcaca | gtagctttaa | tcagtgaaag | tgataggcgt | 600 |
| cgtggactct | ctcaagttct | ttggttgctt | ggtggtgttt | cgggttggat | gtagttttg | 660 |
| tttatgtcca | cgagcaatct | gtgcctaaca | tttctagggt | tcaattcaat | gattcaatcc | 720 |
| aaccaaaaaa | aaaaaaaaaa | aaaaaaaaaa | aaaaaag | | | 757 |

<210> SEQ ID NO 16
<211> LENGTH: 157
<212> TYPE: PRT
<213> ORGANISM: Zea mays

<400> SEQUENCE: 16

Met Gly Lys Gly Val Leu Lys Val His Leu Val Asp Ala Lys Gly Leu
1               5                   10                  15

Ser Gly Asn Asp Phe Leu Gly Lys Leu Asp Pro Tyr Val Ile Met Gln
            20                  25                  30

Tyr Arg Ser Gln Glu Arg Lys Ser Ser Val Ala Arg Asp Gln Gly Arg
        35                  40                  45

Asn Pro Cys Trp Asn Glu Val Phe Lys Phe Gln Ile Asn Ser Ala Ala
    50                  55                  60

Ala Asn Val Gln His Lys Leu Ile Leu Arg Ile Met Asp His Asp Asn
65                  70                  75                  80

Phe Ser Ser Asp Asp Phe Leu Gly Glu Ala Thr Ile Asp Val Thr Asp
                85                  90                  95

Ile Val Ser Leu Gly Ala Glu Arg Gly Thr Tyr His Leu Asn Ala Ala
            100                 105                 110

Lys His Asn Val Val Leu Ala Asp Lys Thr Tyr His Gly Glu Ile Lys
        115                 120                 125

Val Ala Ile Thr Phe Thr Ser Thr Gln Thr Val Gln Glu Asp Gly
    130                 135                 140

Gly Ala Ile Gly Gly Trp Arg His Ser Ser Phe Asn Gln
145                 150                 155

<210> SEQ ID NO 17
<211> LENGTH: 422
<212> TYPE: DNA
<213> ORGANISM: Hevea brasiliensis
<220> FEATURE:

```
<221> NAME/KEY: unsure
<222> LOCATION: (410)
<223> OTHER INFORMATION: n = A, C, G or T
<220> FEATURE:
<221> NAME/KEY: unsure
<222> LOCATION: (415)
<223> OTHER INFORMATION: n = A, C, G or T

<400> SEQUENCE: 17
tcccaatcca cttgctcatt tcccttaagc tctatatata cctttagaaa tttcttcttc      60
ttgatctcca gaggtgtctt attcaatcct aaagcaagat tcaagaaacg gagatggcta     120
ctgggctatt ggaagtgcag ctggtgaatg caaaaggcct cagaggcact gatttcttag     180
gtaagattga tccatatgtt atcgtgaagt acaaaaacca agagcgcgag agcagtgtcg     240
ccagaggtca aggtgggaat ccagtgtgga atgagaaact cacattcaag gtggaatatc     300
cagggcaagg tgaagagtac aagctcattt taaaaatcat ggacaaggac accttctctg     360
ctgatgattt gcttgggcca tgctacgata tatgtgaagg atttgttggn attangaatg     420
ga                                                                   422

<210> SEQ ID NO 18
<211> LENGTH: 102
<212> TYPE: PRT
<213> ORGANISM: Hevea brasiliensis
<220> FEATURE:
<221> NAME/KEY: UNSURE
<222> LOCATION: (99)
<223> OTHER INFORMATION: Xaa = any amino acid
<220> FEATURE:
<221> NAME/KEY: UNSURE
<222> LOCATION: (101)
<223> OTHER INFORMATION: Xaa = any amino acid

<400> SEQUENCE: 18

Met Ala Thr Gly Leu Leu Glu Val Gln Leu Val Asn Ala Lys Gly Leu
  1               5                  10                  15

Arg Gly Thr Asp Phe Leu Gly Lys Ile Asp Pro Tyr Val Ile Val Lys
                 20                  25                  30

Tyr Lys Asn Gln Glu Arg Glu Ser Ser Val Ala Arg Gly Gln Gly Gly
             35                  40                  45

Asn Pro Val Trp Asn Glu Lys Leu Thr Phe Lys Val Glu Tyr Pro Gly
         50                  55                  60

Gln Gly Glu Glu Tyr Lys Leu Ile Leu Lys Ile Met Asp Lys Asp Thr
 65                  70                  75                  80

Phe Ser Ala Asp Asp Leu Leu Gly His Ala Thr Ile Tyr Val Lys Asp
                 85                  90                  95

Leu Leu Xaa Leu Xaa Met
            100

<210> SEQ ID NO 19
<211> LENGTH: 486
<212> TYPE: DNA
<213> ORGANISM: Glycine max
<220> FEATURE:
<221> NAME/KEY: unsure
<222> LOCATION: (430)
<223> OTHER INFORMATION: n = A, C, G or T
<220> FEATURE:
<221> NAME/KEY: unsure
<222> LOCATION: (464)
<223> OTHER INFORMATION: n = A, C, G or T
<220> FEATURE:
<221> NAME/KEY: unsure
<222> LOCATION: (486)
```

<223> OTHER INFORMATION: n = A, C, G or T

<400> SEQUENCE: 19

```
agaagaatag aatcttcaga gacatggcaa ttgggttcat ggaggtgcag cttgtgaaag    60
caaaaggcct gcgagacact gatatctttg gtaaaatgga tccctatgtt ctgatacaat   120
acaaaggcca agaagagg agtggtgtcg ctaatggcaa aggcaaaaat ccggtatgga    180
atgagaaatt tatcttcaaa gtagaatatc ctggatcaag caatcaacac aagctcatcc   240
tcaaaattat ggataaagac ttatatacag acgacttcgt cggagaagca ataatccatg   300
tagggattt attggcccaa ggagtagaga acggaggagc caaattacag actctcaagt    360
atagagtggt tcgtgctaac aagtcttatt gtggtgaaat tgatgttggg tgttactttt   420
accccgaaan gtgggaagac aaattttgtg ggaagaagac atangaggat ggaaaagaaa   480
gtgacn                                                               486
```

<210> SEQ ID NO 20
<211> LENGTH: 154
<212> TYPE: PRT
<213> ORGANISM: Glycine max
<220> FEATURE:
<221> NAME/KEY: UNSURE
<222> LOCATION: (136)
<223> OTHER INFORMATION: Xaa = any amino acid
<220> FEATURE:
<221> NAME/KEY: UNSURE
<222> LOCATION: (147)
<223> OTHER INFORMATION: Xaa = any amino acid

<400> SEQUENCE: 20

```
Met Ala Ile Gly Phe Met Glu Val Gln Leu Val Lys Ala Lys Gly Leu
  1               5                  10                  15

Arg Asp Thr Asp Ile Phe Gly Lys Met Asp Pro Tyr Val Leu Ile Gln
             20                  25                  30

Tyr Lys Gly Gln Glu Lys Arg Ser Gly Val Ala Asn Gly Lys Gly Lys
         35                  40                  45

Asn Pro Val Trp Asn Glu Lys Phe Ile Phe Lys Val Glu Tyr Pro Gly
     50                  55                  60

Ser Ser Asn Gln His Lys Leu Ile Leu Lys Ile Met Asp Lys Asp Leu
 65                  70                  75                  80

Tyr Thr Asp Asp Phe Val Gly Glu Ala Ile Ile His Val Gly Asp Leu
                 85                  90                  95

Leu Ala Gln Gly Val Glu Asn Gly Gly Ala Lys Leu Gln Thr Leu Lys
            100                 105                 110

Tyr Arg Val Val Arg Ala Asn Lys Ser Tyr Cys Gly Glu Ile Asp Val
        115                 120                 125

Gly Cys Tyr Phe Tyr Pro Glu Xaa Trp Glu Asp Lys Phe Cys Gly Lys
    130                 135                 140

Lys Thr Xaa Glu Asp Gly Lys Glu Ser Asp
145                 150
```

<210> SEQ ID NO 21
<211> LENGTH: 862
<212> TYPE: DNA
<213> ORGANISM: Glycine max

<400> SEQUENCE: 21

```
ttattagaca ttaaattgta agaattttgc tgacttgtaa gcttcagaga cgaagacaca    60
cggttagagt gagaaagaga tggcaattgg gttcatggag gtgcagcttg tgaaagcaaa   120
```

```
ggagttgtgt gacactgatt tctttggtag tatggacccg tatgttgtga tacaatacaa    180
cggccaagag caaaggagta gtgttgctaa gggacagggc aataatccgg tatggaatga    240
gaaatttgtg ttcaaggtag aatatcctac actgagtaat tcatacaaga ttatcttaaa    300
aatcatggac aaggatcttt tatctgcaga tgactttgtt ggtcaagcca tagtctatgt    360
ggaagattta ttagccatag gggtagagga tggtgcggct gagctacaac ctctaaagta    420
cagagtaatt cgtgcagatc aatcttattg tggagaaatt gatcttggta taacttttaa    480
ggtggaagaa gagttcaatg gagaagctaa acgaggatcg aaggacagta aatagtattt    540
gcaatagcag ttggccaaca tgaatatcaa ttgatttcaa tggagatttt ggaatcatca    600
tcatgtagtt agtttcatct ttttagttgt atatgatcct tttggaaagt aggatcaatg    660
catagataaa tttactaaat tttatgccat caaattagta atagtatgca ttattaatct    720
tctaatttat cttcaccata attaatctca ttgatgattc aatcttgtac ttccttaaca    780
tctatatact atatgggttt gaacctttaa aaaaaaagaa aaaaaaaaaa aaaaaaaaa    840 aaaaaaaaaa aaaaaaaaaa aa                                             862
```

<210> SEQ ID NO 22
<211> LENGTH: 151
<212> TYPE: PRT
<213> ORGANISM: Glycine max

<400> SEQUENCE: 22

```
Met Ala Ile Gly Phe Met Glu Val Gln Leu Val Lys Ala Lys Glu Leu
  1               5                  10                  15

Cys Asp Thr Asp Phe Phe Gly Ser Met Asp Pro Tyr Val Val Ile Gln
             20                  25                  30

Tyr Asn Gly Gln Glu Gln Arg Ser Ser Val Ala Lys Gly Gln Gly Asn
         35                  40                  45

Asn Pro Val Trp Asn Glu Lys Phe Val Phe Lys Val Glu Tyr Pro Thr
     50                  55                  60

Leu Ser Asn Ser Tyr Lys Ile Ile Leu Lys Ile Met Asp Lys Asp Leu
 65                  70                  75                  80

Leu Ser Ala Asp Asp Phe Val Gly Gln Ala Ile Val Tyr Val Glu Asp
                 85                  90                  95

Leu Leu Ala Ile Gly Val Glu Asp Gly Ala Ala Glu Leu Gln Pro Leu
            100                 105                 110

Lys Tyr Arg Val Ile Arg Ala Asp Gln Ser Tyr Cys Gly Glu Ile Asp
        115                 120                 125

Leu Gly Ile Thr Phe Lys Val Glu Glu Glu Phe Asn Gly Glu Ala Lys
    130                 135                 140

Arg Gly Ser Lys Asp Ser Lys
145                 150
```

<210> SEQ ID NO 23
<211> LENGTH: 860
<212> TYPE: DNA
<213> ORGANISM: Triticum aestivum

<400> SEQUENCE: 23

```
tccaaacgcg acctcatcag agcaagaccc ggaggaaaca aggagaggcc agagcggcct     60
gtcacaaggc aaaggacaga ggaggtgctt gttcaggtct cctgctagat ccggaggcga    120
tgggcagggg cgtgctggag gtgcatctcg tcgacgccaa gggcctcttc ggcagcgatt    180
```

-continued

```
tcctagggaa gatcgacccg tatgtaatcg tgcaataccg gagccaggag cgcaagagca    240
gcacctccag agatgagggg aggaacccga gctggaacga ggtgttccgg ttccagatca    300
actcctctgc ggccaacggg cagcacaagc tcttcctccg gatcatggac cacgacaact    360
tctccagcga cgacttcctc ggccaagcga cgatcaacgt gaccgatctg atcagcaccg    420
gcatggagag cggcgcgtcg cagctgaacg cggcaaagta cagcgttgtg tccgctgata    480
actcatacca cggcgagatc agagtaggcc tcacgttcac cgccaccaag gttgaagaag    540
acggagggca ggtcggaggc tggacgcaca gctctcgcga gtagagcatg taacgtcctt    600
gcccttcgct cgtagcttta gtgttggatg ctatgatgtc cgtgactgaa tgatgtgatt    660
ccaagtgtat gtacgttgca cctgtagtag ctttttagaa gatgtatatg tactagtagc    720
cagaagtcag aactcgtagc aggctagagg cgtcaattcc gttaattaat tgtcgatttg    780
tggttcttat tttaggggga attgtgattc tggatgcgaa caccaaaaaa aaaaaaaaaa    840
aaaaaaaaaa aaaaaaaaaa                                                860
```

```
<210> SEQ ID NO 24
<211> LENGTH: 154
<212> TYPE: PRT
<213> ORGANISM: Triticum aestivum

<400> SEQUENCE: 24

Met Gly Arg Gly Val Leu Glu Val His Leu Val Asp Ala Lys Gly Leu
  1               5                  10                  15

Phe Gly Ser Asp Phe Leu Gly Lys Ile Asp Pro Tyr Val Ile Val Gln
             20                  25                  30

Tyr Arg Ser Gln Glu Arg Lys Ser Ser Thr Ser Arg Asp Glu Gly Arg
         35                  40                  45

Asn Pro Ser Trp Asn Glu Val Phe Arg Phe Gln Ile Asn Ser Ser Ala
     50                  55                  60

Ala Asn Gly Gln His Lys Leu Phe Leu Arg Ile Met Asp His Asp Asn
 65                  70                  75                  80

Phe Ser Ser Asp Asp Phe Leu Gly Gln Ala Thr Ile Asn Val Thr Asp
                 85                  90                  95

Leu Ile Ser Thr Gly Met Glu Ser Gly Ala Ser Gln Leu Asn Ala Ala
            100                 105                 110

Lys Tyr Ser Val Val Ser Ala Asp Asn Ser Tyr His Gly Glu Ile Arg
        115                 120                 125

Val Gly Leu Thr Phe Thr Ala Thr Lys Val Glu Glu Asp Gly Gly Gln
    130                 135                 140

Val Gly Gly Trp Thr His Ser Ser Arg Glu
145                 150
```

```
<210> SEQ ID NO 25
<211> LENGTH: 914
<212> TYPE: DNA
<213> ORGANISM: Oryza sativa

<400> SEQUENCE: 25
cttttggaag aaaagatcac ccaaaaccct atattccata gttgagacac aagatttttt     60
gaagccaagt ttgcgcatta catcaaaggg ttcttttgat gcgaccaatg ctgtgaagag    120
tgtaactagc agtatctcta gcgcttcagg gaagcatgtc gctgacgata caagagaatt    180
tgttggagag ctgaacatta cagtggtaag aggtattcag ttggccgtca gagacatgct    240
aacgagcgat ccatatgttg ttctaacact tggggagcag aaagctcaaa ccactgttaa    300
```

```
accgagtgac ttgaacccag tatggaatga ggtgcttaag atatcaattc ctcgaaatta    360
tggacctctt aaacttgaag tatacgacca tgatacgttc tctgctgatg atatcatggg    420
ggaagcggag atagatcttc aaccaatgat cacagccgtc atggcctttg agatccctc     480 gcgtgttggt gacatgcaaa ttggaaggtg gttcatgacc aaagacaatg ccctggtgaa    540
agatagcact gtcaatgttg tgtcgggcaa ggtaaaacag gaagtgcacc taaagttgca    600
gaatgtagaa tcaggtgaga tggagttaga actggaatgg gttccaatac cctagattaa    660
taaagctcga ttggttctct gccaaaaaaa attactcaag aagcgtcagt tttgtaattt    720
aaatgaatgg cttcaaatcc cgtgtactta ctgaatctct gtcttcaaca ttttggccac    780
ccgaacgaaa ttcgtaaaaa tgccattgta aaatatcatg ttgtaatccg tcggctgcac    840
tcacgaccaa ttatattatt ctttagtgaa gtgtgctttc aacccgttgt cataaaaaaa    900
aaaaaaaaaa aaaa                                                      914
```

<210> SEQ ID NO 26
<211> LENGTH: 217
<212> TYPE: PRT
<213> ORGANISM: Oryza sativa

<400> SEQUENCE: 26

```
Phe Trp Lys Lys Arg Ser Pro Lys Thr Leu Tyr Ser Ile Val Glu Thr
  1               5                  10                  15

Gln Asp Phe Leu Lys Pro Ser Leu Arg Ile Thr Ser Lys Gly Ser Phe
             20                  25                  30

Asp Ala Thr Asn Ala Val Lys Ser Val Thr Ser Ser Ile Ser Ser Ala
         35                  40                  45

Ser Gly Lys His Val Ala Asp Asp Thr Arg Glu Phe Val Gly Glu Leu
     50                  55                  60

Asn Ile Thr Val Val Arg Gly Ile Gln Leu Ala Val Arg Asp Met Leu
 65                  70                  75                  80

Thr Ser Asp Pro Tyr Val Val Leu Thr Leu Gly Glu Gln Lys Ala Gln
                 85                  90                  95

Thr Thr Val Lys Pro Ser Asp Leu Asn Pro Val Trp Asn Glu Val Leu
            100                 105                 110

Lys Ile Ser Ile Pro Arg Asn Tyr Gly Pro Leu Lys Leu Glu Val Tyr
        115                 120                 125

Asp His Asp Thr Phe Ser Ala Asp Asp Ile Met Gly Glu Ala Glu Ile
    130                 135                 140

Asp Leu Gln Pro Met Ile Thr Ala Val Met Ala Phe Gly Asp Pro Ser
145                 150                 155                 160

Arg Val Gly Asp Met Gln Ile Gly Arg Trp Phe Met Thr Lys Asp Asn
                165                 170                 175

Ala Leu Val Lys Asp Ser Thr Val Asn Val Val Ser Gly Lys Val Lys
            180                 185                 190

Gln Glu Val His Leu Lys Leu Gln Asn Val Glu Ser Gly Glu Met Glu
        195                 200                 205

Leu Glu Leu Glu Trp Val Pro Ile Pro
    210                 215
```

<210> SEQ ID NO 27
<211> LENGTH: 770
<212> TYPE: DNA
<213> ORGANISM: Oryza sativa

```
<400> SEQUENCE: 27
ccacgcgtcc ggcctgtgca acatcatcat caagaagaag aagagatcaa cggcaagaag      60
actagcgact agcgagagat cgatcgaaga gaagaggaga gatggtgcac gggaagctgg     120
aggtcctcct cgtctgcgcc aagggcctcg aggacactga cttcttgaac gacatggacc     180
cctacgtgat cctcacctgc cgcactcagg agcagaaaag cagcgttgca aaggagcag      240 gaagcgagcc tgaatggaac gagaccttcg tcttcaccgt ctccgacgat gttccacagc     300
tcaatgtcaa gatcatggac agtgatgcct ctcagctga cgatttcgtc ggtgaagcaa      360
acattcctct ggagcctgtg ttcctggaag gcagccttcc tccagccgtc caccgtgtcg     420
tcaaggagga gaagtactgt ggagagatca aggttgctct caccttcact ccagcagcgg     480
aaactcgcca tcatcacaac cacgagaacg aggggaggg ttacagcagc tggaactgat      540
tgcctgctac taatgagcat caacgagagg agatcttgtc tcaagaatta atgtgcttgt     600
caacaatact ccgtgctatg atgtcctaag aactgaaaca tccatttata tgtatatccc     660
agaccattga cttgctctgc ctaaattttg tatatttttt actacaaaga tgtgatggtg     720
tgaaatccag aatattttta tcgaaaaaaa aaaaaaaaa aaaaaaaag                   770
```

<210> SEQ ID NO 28
<211> LENGTH: 145
<212> TYPE: PRT
<213> ORGANISM: Oryza sativa

<400> SEQUENCE: 28

```
Met Val His Gly Lys Leu Glu Val Leu Leu Val Cys Ala Lys Gly Leu
 1               5                  10                  15

Glu Asp Thr Asp Phe Leu Asn Asp Met Asp Pro Tyr Val Ile Leu Thr
             20                  25                  30

Cys Arg Thr Gln Glu Gln Lys Ser Ser Val Ala Lys Gly Ala Gly Ser
         35                  40                  45

Glu Pro Glu Trp Asn Glu Thr Phe Val Phe Thr Val Ser Asp Asp Val
     50                  55                  60

Pro Gln Leu Asn Val Lys Ile Met Asp Ser Asp Ala Phe Ser Ala Asp
 65                  70                  75                  80

Asp Phe Val Gly Glu Ala Asn Ile Pro Leu Glu Pro Val Phe Leu Glu
                 85                  90                  95

Gly Ser Leu Pro Pro Ala Val His Arg Val Val Lys Glu Glu Lys Tyr
            100                 105                 110

Cys Gly Glu Ile Lys Val Ala Leu Thr Phe Thr Pro Ala Ala Glu Thr
        115                 120                 125

Arg His His His Asn His Glu Asn Glu Gly Glu Gly Tyr Ser Ser Trp
    130                 135                 140

Asn
145
```

<210> SEQ ID NO 29
<211> LENGTH: 958
<212> TYPE: DNA
<213> ORGANISM: Glycine max

<400> SEQUENCE: 29

```
gcacagaaag aaaaaagttg gatccagcca aattccagct ccaatttgta actcactgct      60
tcaggcattt ctggcacaat tttttccacc tttatttcaa ctttaagact ccacagaaag     120
aagcatattc ctgagtcaaa tagttctgtc catatagaat ttgtgaagtg agagtccaac     180
```

-continued

```
ctttcatttt caattttcaa agatgcctcg tggaacactt gaagttgttc tgatcagcgc        240
caaaggaatc gatgacaatg attttctctc cagcatagat ccttatgtga ttctcacata        300
cagggcacag gagaaaaaga gcactgtgca agaagatgct ggatccaagc cacaatggaa        360
tgagagcttt cttttcactg tctctgacag tgcttctgaa cttaatctga agataatgga        420
taaagacaac tttagtcaag atgattgtct tggcgaggca accattcatt tagatccagt        480
gtttgaagcc ggtagcattc cagaaactgc ttacaaggtt gtgaaggacg aagaatattg        540
tggtgagatt aaggtggctc tcactttcac tgctgagaga atgaggagc agggttatga         600 tgcacctgaa gagagctatg gtggatggaa agaatccagt ggggaatatt aaagtgaaag        660
aagaatttac atacttcaat ggccagactt acctttataa tgaaaaataa gcagttttgg        720
tgtcactctt aggcaatttc cattattgtg ttttctggtg tgaagatcca atagtgttgt        780
gcttttaggt tgcattcctc cctttggata ttaaagtaca ttatgcttga tatattatct        840
tttatgcatc agttaaacat tagaagagca gtgctatttt atttaaaaaa aaaaaaaaaa        900
aaaaaaaaaa aaaaaaaaaa aaaaaaaaaa aaaaaaaaaa aaaaaaaaaa aaaaaaa          958
```

<210> SEQ ID NO 30
<211> LENGTH: 149
<212> TYPE: PRT
<213> ORGANISM: Glycine max

<400> SEQUENCE: 30

```
Met Pro Arg Gly Thr Leu Glu Val Val Leu Ile Ser Ala Lys Gly Ile
  1               5                  10                  15

Asp Asp Asn Asp Phe Leu Ser Ser Ile Asp Pro Tyr Val Ile Leu Thr
                 20                  25                  30

Tyr Arg Ala Gln Glu Lys Lys Ser Thr Val Gln Glu Asp Ala Gly Ser
             35                  40                  45

Lys Pro Gln Trp Asn Glu Ser Phe Leu Phe Thr Val Ser Asp Ser Ala
         50                  55                  60

Ser Glu Leu Asn Leu Lys Ile Met Asp Lys Asp Asn Phe Ser Gln Asp
 65                  70                  75                  80

Asp Cys Leu Gly Glu Ala Thr Ile His Leu Asp Pro Val Phe Glu Ala
                 85                  90                  95

Gly Ser Ile Pro Glu Thr Ala Tyr Lys Val Val Lys Asp Glu Glu Tyr
                100                 105                 110

Cys Gly Glu Ile Lys Val Ala Leu Thr Phe Thr Ala Glu Arg Asn Glu
            115                 120                 125

Glu Gln Gly Tyr Asp Ala Pro Glu Glu Ser Tyr Gly Gly Trp Lys Glu
        130                 135                 140

Ser Ser Gly Glu Tyr
145
```

<210> SEQ ID NO 31
<211> LENGTH: 695
<212> TYPE: DNA
<213> ORGANISM: Triticum aestivum

<400> SEQUENCE: 31

```
gcacgaggag agatccaaga ctaggccggc cggccggagg agatcgagaa ggaggaggag         60
acatggtgcg cgggaagctg gaggtgctgc tcgtctccgc caagggcctc gacgactccg        120
atttcttcaa tagcatggac ccgtacgtga tcctcacctg ccgcagccac gagcagaaga        180
```

-continued

```
gcaccgtcgc atcaggagca gggagcgagc ctgagtggaa cgagaccttc gtcttcgccg    240
tctccggcga cgctccggag ctcagggtca agatcatgga cagcgacgcc ctctcggccg    300
acgacctcgt cggagaagca tgtatcccgc tggaggctgt gctccaggag ggcagcctgc    360
cgccggccgt gcaccgggtc gtcaaggacg aggagtaccg cggggagatc aagatcgcgc    420
tcaccttcac cccggcagag gaaaacgagg aggaggagga gagctacggc ggctggaatc    480
agtccacctg aaaaaggcca gcgagccagc aagatggtgc tgtatgtctg actgtcataa    540
tggatagaaa ggctttggat atccttgatg tgtgtgacag acagggcatt caggaaaacg    600
agtaaaaata ggggaaatat gtatcgatgc atgcatgaag tactaatcaa gcaattcacc    660
gcatcgtttt gtattgcaaa aaaaaaaaaa aaaaa                               695
```

<210> SEQ ID NO 32
<211> LENGTH: 142
<212> TYPE: PRT
<213> ORGANISM: Triticum aestivum

<400> SEQUENCE: 32

```
Met Val Arg Gly Lys Leu Glu Val Leu Leu Val Ser Ala Lys Gly Leu
  1               5                  10                  15

Asp Asp Ser Asp Phe Phe Asn Ser Met Asp Pro Tyr Val Ile Leu Thr
                 20                  25                  30

Cys Arg Ser His Glu Gln Lys Ser Thr Val Ala Ser Gly Ala Gly Ser
             35                  40                  45

Glu Pro Glu Trp Asn Glu Thr Phe Val Phe Ala Val Ser Gly Asp Ala
         50                  55                  60

Pro Glu Leu Arg Val Lys Ile Met Asp Ser Asp Ala Leu Ser Ala Asp
 65                  70                  75                  80

Asp Leu Val Gly Glu Ala Cys Ile Pro Leu Glu Ala Val Leu Gln Glu
                 85                  90                  95

Gly Ser Leu Pro Pro Ala Val His Arg Val Val Lys Asp Glu Glu Tyr
            100                 105                 110

Arg Gly Glu Ile Lys Ile Ala Leu Thr Phe Thr Pro Ala Glu Glu Asn
        115                 120                 125

Glu Glu Glu Glu Glu Ser Tyr Gly Gly Trp Asn Gln Ser Thr
    130                 135                 140
```

<210> SEQ ID NO 33
<211> LENGTH: 617
<212> TYPE: DNA
<213> ORGANISM: Zea mays
<220> FEATURE:
<221> NAME/KEY: unsure
<222> LOCATION: (421)
<223> OTHER INFORMATION: n = A, C, G or T

<400> SEQUENCE: 33

```
cacgccgcct ccatgtgggt ggggaggcaa acgcgttcgt ccatctctga aactcaaacg     60
ccttgtattg gagcatacta caggagtact tctgtacaaa tataaatacc cctggcgagt    120
tgggttgggt ctatctcgca atcgaggcgt ttttttttctg cttcgtaagt tcgtggtcga    180
tccagcgagc gagcgagcag accggcggcc aaccgcggag ggagagatgg cgcaggggac    240
gctggaggtg cttctcgtcg gagccagggg cctcgagaac accgattacc tgagcaacat    300
ggacccctac gcgcttctgc aatgtcgctc ccacgagcag aagagcagcg tcgcatctgg    360
caaaggctgt gaacctgagt ggaacgagac cttcgtgttc accgtctcca acggcgcaca    420
```

```
ngagctgttc atcaagctcc tggacagtga cggtggcact gatgacgatt ttgttggtga      480
agcaacgatt cctctggaag ccagtttaca cgggaaggaa gcattccttc cgactgttta      540
caatgttgtg aaagacgaag aataccgcgg agaaatcaaa gttggcctca cgttcactcc      600
agaggtaaac catctca                                                    617
```

```
<210> SEQ ID NO 34
<211> LENGTH: 202
<212> TYPE: PRT
<213> ORGANISM: Zea mays
<220> FEATURE:
<221> NAME/KEY: UNSURE
<222> LOCATION: (140)
<223> OTHER INFORMATION: Xaa = any amino acid

<400> SEQUENCE: 34
```

Thr Pro Pro Pro Cys Gly Trp Gly Gly Lys Arg Val Arg Pro Ser Leu
 1               5                  10                  15

Lys Leu Lys Arg Leu Val Leu Glu His Thr Thr Gly Val Leu Leu Tyr
            20                  25                  30

Lys Tyr Lys Tyr Pro Trp Arg Val Gly Leu Gly Leu Ser Arg Asn Arg
        35                  40                  45

Gly Val Phe Phe Leu Leu Arg Lys Phe Val Val Asp Pro Ala Ser Glu
    50                  55                  60

Arg Ala Asp Arg Arg Pro Thr Ala Glu Gly Glu Met Ala Gln Gly Thr
65                  70                  75                  80

Leu Glu Val Leu Leu Val Gly Ala Arg Gly Leu Glu Asn Thr Asp Tyr
                85                  90                  95

Leu Ser Asn Met Asp Pro Tyr Ala Leu Leu Gln Cys Arg Ser His Glu
            100                 105                 110

Gln Lys Ser Ser Val Ala Ser Gly Lys Gly Cys Glu Pro Glu Trp Asn
        115                 120                 125

Glu Thr Phe Val Phe Thr Val Ser Asn Gly Ala Xaa Glu Leu Phe Ile
    130                 135                 140

Lys Leu Leu Asp Ser Asp Gly Gly Thr Asp Asp Asp Phe Val Gly Glu
145                 150                 155                 160

Ala Thr Ile Pro Leu Glu Ala Ser Leu His Gly Lys Glu Ala Phe Leu
                165                 170                 175

Pro Thr Val Tyr Asn Val Val Lys Asp Glu Glu Tyr Arg Gly Glu Ile
            180                 185                 190

Lys Val Gly Leu Thr Phe Thr Pro Glu Val
        195                 200

```
<210> SEQ ID NO 35
<211> LENGTH: 544
<212> TYPE: DNA
<213> ORGANISM: Zea mays
<220> FEATURE:
<221> NAME/KEY: unsure
<222> LOCATION: (415)
<223> OTHER INFORMATION: n = A, C, G or T
<220> FEATURE:
<221> NAME/KEY: unsure
<222> LOCATION: (478)
<223> OTHER INFORMATION: n = A, C, G or T
<220> FEATURE:
<221> NAME/KEY: unsure
<222> LOCATION: (494)
<223> OTHER INFORMATION: n = A, C, G or T
<220> FEATURE:
<221> NAME/KEY: unsure
<222> LOCATION: (509)
```

```
<223> OTHER INFORMATION: n = A, C, G or T
<220> FEATURE:
<221> NAME/KEY: unsure
<222> LOCATION: (515)
<223> OTHER INFORMATION: n = A, C, G or T
<220> FEATURE:
<221> NAME/KEY: unsure
<222> LOCATION: (531)..(532)
<223> OTHER INFORMATION: n = A, C, G or T
<220> FEATURE:
<221> NAME/KEY: unsure
<222> LOCATION: (542)
<223> OTHER INFORMATION: n = A, C, G or T

<400> SEQUENCE: 35
gttcgttcac gccacaggca aggcacaggg gcttgtgagg gagagcgagg agcggaggag      60
gacatggtgc acgggacgct ggaagtgctg ctcgttgggg ccaagggcct cgagaacacc     120
gattacctct gtaacatgga tccgtatgca attctcaagt gccgttcaca ggagcagaag     180
agcagtattg caactggaaa aggaactacc cctgagtgga tgaaaactt tatcttcact      240
gtgtctgacc ggacaacaga cttggtaatc aagcttatgg acagtgatac aggcacagca     300
gatgactttg ttggtgaagc aacgattcca ttggaagcag tgtatactga aggagcatt     360
ccaccaacac tctataatgt tgtgaaaggt gaaaaatact gcggggaaat caaantggtc    420
tcacattcac tcctgaggat actcgcaagc gggtctccaa aggacttcgt ggtgaanca     480
tcatcttaag ctantcttta gggtcacana cacancacaa tcatcgcttg nncctcaccg    540
tnat                                                                 544

<210> SEQ ID NO 36
<211> LENGTH: 130
<212> TYPE: PRT
<213> ORGANISM: Zea mays
<220> FEATURE:
<221> NAME/KEY: UNSURE
<222> LOCATION: (118)
<223> OTHER INFORMATION: Xaa = any amino acid

<400> SEQUENCE: 36

Met Val His Gly Thr Leu Glu Val Leu Leu Val Gly Ala Lys Gly Leu
  1               5                  10                  15

Glu Asn Thr Asp Tyr Leu Cys Asn Met Asp Pro Tyr Ala Ile Leu Lys
             20                  25                  30

Cys Arg Ser Gln Glu Gln Lys Ser Ser Ile Ala Thr Gly Lys Gly Thr
         35                  40                  45

Thr Pro Glu Trp Asn Glu Asn Phe Ile Phe Thr Val Ser Asp Arg Thr
     50                  55                  60

Thr Asp Leu Val Ile Lys Leu Met Asp Ser Asp Thr Gly Thr Ala Asp
 65                  70                  75                  80

Asp Phe Val Gly Glu Ala Thr Ile Pro Leu Glu Ala Val Tyr Thr Glu
                 85                  90                  95

Arg Ser Ile Pro Pro Thr Leu Tyr Asn Val Val Lys Gly Glu Lys Tyr
            100                 105                 110

Cys Gly Glu Ile Lys Xaa Gly Leu Thr Phe Thr Pro Glu Asp Thr Arg
        115                 120                 125

Lys Arg
    130

<210> SEQ ID NO 37
<211> LENGTH: 459
<212> TYPE: DNA
```

<213> ORGANISM: Triticum aestivum
<220> FEATURE:
<221> NAME/KEY: unsure
<222> LOCATION: (435)
<223> OTHER INFORMATION: n = A, C, G or T

<400> SEQUENCE: 37

```
gccgagcttt ccattttcca actcctagtc ctatacatac agcggaaccc cggggctcgg      60
atcggatcta cagcaattag tctcgacctt cagtcgtgcc gcctgctcat cagcatataa     120
ttcctgatcg agcgagcggg agaggaaggc gagatcaggc cgggagagaa gatggcgcag     180
gggacgctgg aggtgctgct cgtgggagcc aagggcctcg agaacaccga ctacctctgc     240
aacatggacc cgtacgcggt tctaaaatgc acctcgcagg agcaaaagag caccgtcgcc     300
tctggaaagg gaagtgatcc tgagtggaac gaaacctttg tgttcaccgt ctctgagaat     360
gcaactgagc ttgtcatcaa gctactggac agtgatggtg gcacggacga cgacagcgtt     420
ggtgaagcaa cgatncattg gatggagtgt acactgaag                           459
```

<210> SEQ ID NO 38
<211> LENGTH: 87
<212> TYPE: PRT
<213> ORGANISM: Triticum aestivum

<400> SEQUENCE: 38

```
Met Ala Gln Gly Thr Leu Glu Val Leu Leu Val Gly Ala Lys Gly Leu
 1               5                  10                  15

Glu Asn Thr Asp Tyr Leu Cys Asn Met Asp Pro Tyr Ala Val Leu Lys
            20                  25                  30

Cys Thr Ser Gln Glu Gln Lys Ser Thr Val Ala Ser Gly Lys Gly Ser
        35                  40                  45

Asp Pro Glu Trp Asn Glu Thr Phe Val Phe Thr Val Ser Glu Asn Ala
    50                  55                  60

Thr Glu Leu Val Ile Lys Leu Leu Asp Ser Asp Gly Gly Thr Asp Asp
65                  70                  75                  80

Asp Ser Val Gly Glu Ala Thr
                85
```

<210> SEQ ID NO 39
<211> LENGTH: 417
<212> TYPE: DNA
<213> ORGANISM: Oryza sativa

<400> SEQUENCE: 39

```
atcgtcaact cagctcctct ctttcttccc ctccccgct cctccgcgag acgacccgcg       60
cccgtagcca tccatgtcga tacaaggcca gatcctcgaa gtcagagtca ctgggtgcag     120
gaagctgagg gacacggagt tcttcacgcg gcaggatccc tacgtctgca tcgagtatgc     180
caccaacaag ttccgcaccc gcacctgcac cgatggggga aggaacccta cttttgacga     240
gaagtttcat atacctctca ttgaggggct tcgtgagcta accgtcacag tgtggaacag     300
caacacgctc acccatgatg atttcattgg caatggcagg gtgcaagctg cataaggtgc     360
ttacgcgtgg ctatgatgat gcctcaaggg ccctccagac acgccatatg aggtctg       417
```

<210> SEQ ID NO 40
<211> LENGTH: 83
<212> TYPE: PRT
<213> ORGANISM: Oryza sativa

<400> SEQUENCE: 40

Leu Glu Val Arg Val Thr Gly Cys Arg Lys Leu Arg Asp Thr Glu Phe
1               5                   10                  15

Phe Thr Arg Gln Asp Pro Tyr Val Cys Ile Glu Tyr Ala Thr Asn Lys
                20                  25                  30

Phe Arg Thr Arg Thr Cys Thr Asp Gly Gly Arg Asn Pro Thr Phe Asp
            35                  40                  45

Glu Lys Phe His Ile Pro Leu Ile Glu Gly Leu Arg Glu Leu Thr Val
        50                  55                  60

Thr Val Trp Asn Ser Asn Thr Leu Thr His Asp Asp Phe Ile Gly Asn
65                  70                  75                  80

Gly Arg Val

<210> SEQ ID NO 41
<211> LENGTH: 550
<212> TYPE: DNA
<213> ORGANISM: Glycine max
<220> FEATURE:
<221> NAME/KEY: unsure
<222> LOCATION: (534)
<223> OTHER INFORMATION: n = A, C, G or T

<400> SEQUENCE: 41
ggtgaattgc aatttcaatt aattagaatt caacgtttgc aaattgcata ttgttcttct      60
cttcctctct tcctctgact ccatgtcgtc gataacgggc atccagggcc aacctcttga     120
ggttacggtg gtttcgtgct ccaagttgaa ggacacagaa tggatttcaa ggcaagatcc     180
gtacgtttgt gttgagtatg gcagcacaaa gttccgaacc agaacctgca cagacggcgg     240
aaaaaatccg gtattccaag agaagttcat cttcccccct cattgaaggc cttcgggagct    300
caatgtcctt gtttggaaca gcaatactct caccttggac gattttatag gaagcggaaa    360
gattcaattg cacaaggttc tctctcaagg cttcgatgac tctgcttggc cacttcagac    420
caaaactggc agatacgctg gtgaagtcaa agtcatattg cattacgcaa ttgcaaatca    480
tcaaaggcat aaatcagtgt caagccatgc tccatcaaca cctccgtatg tggnaacaac    540
aactcctccc                                                           550

<210> SEQ ID NO 42
<211> LENGTH: 116
<212> TYPE: PRT
<213> ORGANISM: Glycine max

<400> SEQUENCE: 42

Met Ser Ser Ile Thr Gly Ile Gln Gly Gln Pro Leu Glu Val Thr Val
1               5                   10                  15

Val Ser Cys Ser Lys Leu Lys Asp Thr Glu Trp Ile Ser Arg Gln Asp
                20                  25                  30

Pro Tyr Val Cys Val Glu Tyr Gly Ser Thr Lys Phe Arg Thr Arg Thr
            35                  40                  45

Cys Thr Asp Gly Gly Lys Asn Pro Val Phe Gln Glu Lys Phe Ile Phe
        50                  55                  60

Pro Leu Ile Glu Gly Leu Arg Glu Leu Asn Val Leu Trp Asn Ser
65                  70                  75                  80

Asn Thr Leu Thr Leu Asp Asp Phe Ile Gly Ser Gly Lys Ile Gln Leu
                85                  90                  95

His Lys Val Leu Ser Gln Gly Phe Asp Asp Ser Ala Trp Pro Leu Gln
            100                 105                 110

-continued

```
Thr Lys Thr Gly
        115

<210> SEQ ID NO 43
<211> LENGTH: 424
<212> TYPE: DNA
<213> ORGANISM: Zea mays
<220> FEATURE:
<221> NAME/KEY: unsure
<222> LOCATION: (169)..(170)
<223> OTHER INFORMATION: n = A, C, G or T
<220> FEATURE:
<221> NAME/KEY: unsure
<222> LOCATION: (172)..(173)
<223> OTHER INFORMATION: n = A, C, G or T
<220> FEATURE:
<221> NAME/KEY: unsure
<222> LOCATION: (178)..(179)..(180)
<223> OTHER INFORMATION: n = A, C, G or T
<220> FEATURE:
<221> NAME/KEY: unsure
<222> LOCATION: (183)
<223> OTHER INFORMATION: n = A, C, G or T

<400> SEQUENCE: 43
acccacgcgt ccgcccacgc gtccgccgcg ccgccgcaag agaggagaga gcgcctccaa      60
cgccacctgg aggagaggac agcgcgccag ggaggggggag gaggaagaag aacatgggga   120
agggcgtcct gaaggtgcac ctcgtcgacg ccaagggggct ctccggcann gnntctnnn   180 ggnagctgga cccctacgtg atcatgcagt accggagcca ggagcgcaag agcagcgtcg   240
cccgagacca aggaaggaac ccgtgctgga acgaggtgtt caagttccag atcaactcgg   300
ccgcggccaa cgtgcagcac aagctcatcc tccggatcat ggaccacgac aacttctcca   360
gcgacgactt ctcggcgagg cgacgatcga cgtgacggac atcgtcagcc tgggcgccga   420
gcgc                                                                 424

<210> SEQ ID NO 44
<211> LENGTH: 85
<212> TYPE: PRT
<213> ORGANISM: Zea mays
<220> FEATURE:
<221> NAME/KEY: UNSURE
<222> LOCATION: (18)..(19)
<223> OTHER INFORMATION: Xaa = any amino acid
<220> FEATURE:
<221> NAME/KEY: UNSURE
<222> LOCATION: (21)..(22)..(23)
<223> OTHER INFORMATION: Xaa = any amino acid

<400> SEQUENCE: 44

Gly Lys Gly Val Leu Lys Val His Leu Val Asp Ala Lys Gly Leu Ser
 1               5                  10                  15

Gly Xaa Xaa Phe Xaa Xaa Xaa Leu Asp Pro Tyr Val Ile Met Gln Tyr
             20                  25                  30

Arg Ser Gln Glu Arg Lys Ser Ser Val Ala Arg Asp Gln Gly Arg Asn
         35                  40                  45

Pro Cys Trp Asn Glu Val Phe Lys Phe Gln Ile Asn Ser Ala Ala Ala
     50                  55                  60

Asn Val Gln His Lys Leu Ile Leu Arg Ile Met Asp His Asp Asn Phe
 65                  70                  75                  80

Ser Ser Asp Asp Phe
                 85

<210> SEQ ID NO 45
```

```
<211> LENGTH: 548
<212> TYPE: DNA
<213> ORGANISM: Glycine max
<220> FEATURE:
<221> NAME/KEY: unsure
<222> LOCATION: (291)
<223> OTHER INFORMATION: n = A, C, G or T
<220> FEATURE:
<221> NAME/KEY: unsure
<222> LOCATION: (349)
<223> OTHER INFORMATION: n = A, C, G or T
<220> FEATURE:
<221> NAME/KEY: unsure
<222> LOCATION: (417)
<223> OTHER INFORMATION: n = A, C, G or T
<220> FEATURE:
<221> NAME/KEY: unsure
<222> LOCATION: (437)
<223> OTHER INFORMATION: n = A, C, G or T
<220> FEATURE:
<221> NAME/KEY: unsure
<222> LOCATION: (446)
<223> OTHER INFORMATION: n = A, C, G or T
<220> FEATURE:
<221> NAME/KEY: unsure
<222> LOCATION: (486)
<223> OTHER INFORMATION: n = A, C, G or T
<220> FEATURE:
<221> NAME/KEY: unsure
<222> LOCATION: (492)
<223> OTHER INFORMATION: n = A, C, G or T
<220> FEATURE:
<221> NAME/KEY: unsure
<222> LOCATION: (506)
<223> OTHER INFORMATION: n = A, C, G or T
<220> FEATURE:
<221> NAME/KEY: unsure
<222> LOCATION: (525)
<223> OTHER INFORMATION: n = A, C, G or T
<220> FEATURE:
<221> NAME/KEY: unsure
<222> LOCATION: (528)
<223> OTHER INFORMATION: n = A, C, G or T
<220> FEATURE:
<221> NAME/KEY: unsure
<222> LOCATION: (544)
<223> OTHER INFORMATION: n = A, C, G or T

<400> SEQUENCE: 45
ttaaattgta agaattttgc tgacttgtaa gcttcagaga cgaagacaca cggttagagt      60
gagaaagaga tggcaattgg gttcatggag gtgcagcttg tgaaagcaaa ggagttgtgt     120
gacactgatt tctttggtag tatggacccg tatgttgtga tacaatacaa cggccaagag     180
caaaggagta gtgttgctaa gggacagggc aataatccgg tatggaatga gaaatttgtg     240
ttcaaggtag aatatcctac actgagtaat tcatacaaga ttatcttaaa natcatggac     300
aaggatcttt tatctgcaga tgactttgtt ggtcaagcca tagtcctang tgggaagatt     360
tattagccat aagggggtaga ggatggtgcc ggctgagcta caacctccta agtacnaga      420 gtaattccgt gcagatnaat ccttantggt ggagaaattg atcttgggat aacttttaaa     480
gggggnaaga angagttcaa tggagnaagc ctaaaccaag gatcnaaggg acagtaaatt    540 agtntttc                                                               548

<210> SEQ ID NO 46
<211> LENGTH: 89
<212> TYPE: PRT
<213> ORGANISM: Glycine max
<220> FEATURE:
<221> NAME/KEY: UNSURE
<222> LOCATION: (71)
<223> OTHER INFORMATION: Xaa = ANY AMINO ACID
```

<400> SEQUENCE: 46

Gly Phe Met Glu Val Gln Leu Val Lys Ala Lys Glu Leu Cys Asp Thr
 1               5                  10                  15

Asp Phe Phe Gly Ser Met Asp Pro Tyr Val Val Ile Gln Tyr Asn Gly
            20                  25                  30

Gln Glu Gln Arg Ser Ser Val Ala Lys Gly Gln Gly Asn Asn Pro Val
        35                  40                  45

Trp Asn Glu Lys Phe Val Phe Lys Val Glu Tyr Pro Thr Leu Ser Asn
    50                  55                  60

Ser Tyr Lys Ile Ile Leu Xaa Ile Met Asp Lys Asp Leu Leu Ser Ala
65                  70                  75                  80

Asp Asp Phe Val Gly Gln Ala Ile Val
                85

<210> SEQ ID NO 47
<211> LENGTH: 473
<212> TYPE: DNA
<213> ORGANISM: Triticum aestivum
<220> FEATURE:
<221> NAME/KEY: unsure
<222> LOCATION: (296)
<223> OTHER INFORMATION: n=a,c,g or t
<220> FEATURE:
<221> NAME/KEY: unsure
<222> LOCATION: (473)
<223> OTHER INFORMATION: n=a,c,g or t

<400> SEQUENCE: 47
tccaaacgcg acctcatcag agcaagaccc ggaggaaaca aggagaggcc agagcggcct      60
gtcacaaggc aaggacagag gaggtgcttg ttcaggtctc ctgctagatc cggaggcgat     120
gggcaggggc tgctggaggt gcatctcgtc gacgccaagg gcctcttcgg cagcgatttc     180
ctaggaagat cgacccgtat gtaatcgtgc aataccggag ccaggagcgc aagagcagca     240
ctccagagat gagggagga acccgagctg gaacgaggtg ttccggttcc agatcnctcc     300
tctgcggcca acgggcagca caagctcttc ctccggatca tggaccacga catcttctcc     360
agcgacgact cctcggcca gcgacgatc aacgtgaccg atctgatcag accggcatgg     420
agaagcgggc gcgtcgcagc tgaacgcggc aaagtacaac gttgttgtcc gcn            473

<210> SEQ ID NO 48
<211> LENGTH: 99
<212> TYPE: PRT
<213> ORGANISM: Triticum aestivum
<220> FEATURE:
<221> NAME/KEY: UNSURE
<222> LOCATION: (24)
<223> OTHER INFORMATION: Xaa = ANY AMINO ACID
<220> FEATURE:
<221> NAME/KEY: UNSURE
<222> LOCATION: (47)
<223> OTHER INFORMATION: Xaa = ANY AMINO ACID
<220> FEATURE:
<221> NAME/KEY: UNSURE
<222> LOCATION: (62)
<223> OTHER INFORMATION: Xaa = ANY AMINO ACID

<400> SEQUENCE: 48

Gly Gln Gly Leu Leu Glu Val His Leu Val Asp Ala Lys Gly Leu Phe
 1               5                  10                  15

Gly Ser Asp Phe Leu Gly Arg Xaa Asp Pro Tyr Val Ile Val Gln Tyr
            20                  25                  30

-continued

Arg Ser Gln Glu Arg Lys Ser Ser Thr Pro Glu Met Arg Gly Xaa Gly
         35                  40                  45

Glu Glu Pro Glu Leu Glu Arg Gly Val Pro Val Pro Asp Xaa Ser Ser
     50                  55                  60

Ala Ala Asn Gly Gln His Lys Leu Phe Leu Arg Ile Met Asp His Asp
 65                  70                  75                  80

Ile Phe Ser Ser Asp Asp Phe Leu Gly Gln Ala Thr Ile Asn Val Thr
             85                  90                  95

Asp Leu Ile

<210> SEQ ID NO 49
<211> LENGTH: 465
<212> TYPE: DNA
<213> ORGANISM: Oryza sativa

<400> SEQUENCE: 49
aaagatcacc caaaaccta tattccatag ttgagacaca agattttttg aagccaagtt      60
tgcgcattac atcaaagggt tcttttgatg cgaccaatgc tgtgaagagt gtaactagca    120
gtatctctag cgcttcaggg aagcatgtcg ctgacgatac aagagaattt gttggagagc    180
tgaacattac agtggtaaga ggtattcaag ttggccgtca gagacatgct aacgagcgat    240
ccatatgttg ttctaacact tggggagcag aaagctcaaa ccactgttaa accgagtgac    300
ttgaacccag tatggaatga ggtgcttaag atatcaattc ctcgaaatta tggacctctt    360
aaacttgaag tatacgacca tgatacgttc tctgctgatg atatcatggg ggaagcggag    420
atagatcttc aaccaatgat cacagccgtc atggcctttg gagaa                    465

<210> SEQ ID NO 50
<211> LENGTH: 31
<212> TYPE: PRT
<213> ORGANISM: Oryza sativa

<400> SEQUENCE: 50

Val Val Leu Thr Leu Gly Glu Gln Lys Ala Gln Thr Thr Val Lys Pro
 1               5                  10                  15

Ser Asp Leu Asn Pro Val Trp Asn Glu Val Leu Lys Ile Ser Ile
             20                  25                  30

<210> SEQ ID NO 51
<211> LENGTH: 390
<212> TYPE: DNA
<213> ORGANISM: Oryza sativa
<220> FEATURE:
<221> NAME/KEY: unsure
<222> LOCATION: (43)
<223> OTHER INFORMATION: n=a,c,g or t
<220> FEATURE:
<221> NAME/KEY: unsure
<222> LOCATION: (204)
<223> OTHER INFORMATION: n=a,c,g or t
<220> FEATURE:
<221> NAME/KEY: unsure
<222> LOCATION: (301)
<223> OTHER INFORMATION: n=a,c,g or t
<220> FEATURE:
<221> NAME/KEY: unsure
<222> LOCATION: (347)
<223> OTHER INFORMATION: n=a,c,g or t
<220> FEATURE:
<221> NAME/KEY: unsure
<222> LOCATION: (373)
<223> OTHER INFORMATION: n=a,c,g or t

<400> SEQUENCE: 51

```
gcctgtgcaa catcatcatc aagaagaaga agagatcaac ggnaagaaga ctagcgacta        60
gcgagagatc gatcgaagag aagaggagag atggtgcacg ggaagctgga ggtcctcctc       120
gtctgcgcca agggcctcga ggacactgac ttcttgaacg acatggaccc ctacgtgatc       180
ctcacctgcc gcactcagga gcangaaaag cagcgttgca aaaggagcag gaagcgagcc       240
tgaatggaac gagaccttcg tcttcaccgt ctccgacgat gttccacagc tcaatgtcaa       300
ngatcatgga caagtgatgg ccttctcaag ctgacgattt cggtccnggt gaagcaaaca       360
attcctctgg gangcctgtg ttcctgggaa                                         390
```

<210> SEQ ID NO 52
<211> LENGTH: 69
<212> TYPE: PRT
<213> ORGANISM: Oryza sativa

<400> SEQUENCE: 52

```
Met Val His Gly Lys Leu Glu Val Leu Val Cys Ala Lys Gly Leu
  1               5                  10                  15

Glu Asp Thr Asp Phe Leu Asn Asp Met Asp Pro Tyr Val Ile Leu Thr
                 20                  25                  30

Cys Arg Thr Gln Glu Gln Lys Ser Ser Val Ala Lys Gly Ala Gly Ser
             35                  40                  45

Glu Pro Glu Trp Asn Glu Thr Phe Val Phe Thr Val Ser Asp Asp Val
     50                  55                  60

Pro Gln Leu Asn Val
 65
```

<210> SEQ ID NO 53
<211> LENGTH: 489
<212> TYPE: DNA
<213> ORGANISM: Glycine max
<220> FEATURE:
<221> NAME/KEY: unsure
<222> LOCATION: (417)
<223> OTHER INFORMATION: n=a,c,g or t
<220> FEATURE:
<221> NAME/KEY: unsure
<222> LOCATION: (428)
<223> OTHER INFORMATION: n=a,c,g or t
<220> FEATURE:
<221> NAME/KEY: unsure
<222> LOCATION: (452)
<223> OTHER INFORMATION: n=a,c,g or t
<220> FEATURE:
<221> NAME/KEY: unsure
<222> LOCATION: (482)
<223> OTHER INFORMATION: n=a,c,g or t

<400> SEQUENCE: 53

```
agaaagaaaa aagtggatcc agccaaattc cagctccaat ttgtaactca ctgcttcagg        60
catttctggc acaattttttt ccacctttat ttcaacttta agactccaca gaaagaagca      120
tattcctgag tcaaatagtt ctgtccatat agaatttgtg aagtgagagt ccaacctttc      180
attttcaatt ttcaaagatg cctcgtggaa cacttgaagt tgttctgatc agcgccaaag      240
gaatcgatga caatgatttt ctctccagca tagatcctta tgtgattctc acatacaggg      300
cacaggagaa aaagagcact gtgcaagaaa gatgctggat ccaagccaca atggaatgag      360 agcttttcttt tcactgtctc tgacagtgct tctgaactta atctgaagat aatgggntaa     420
agacaacntt agtcaaagat ggttggcctg gngagggaac caatcaatta gattcaagtg      480 gnttggagg                                                              489
```

<210> SEQ ID NO 54
<211> LENGTH: 42
<212> TYPE: PRT
<213> ORGANISM: Glycine max

<400> SEQUENCE: 54

Met Pro Arg Gly Thr Leu Glu Val Val Leu Ile Ser Ala Lys Gly Ile
1               5                   10                  15

Asp Asp Asn Asp Phe Leu Ser Ser Ile Asp Pro Tyr Val Ile Leu Thr
            20                  25                  30

Tyr Arg Ala Gln Glu Lys Lys Ser Thr Val
        35                  40

<210> SEQ ID NO 55
<211> LENGTH: 523
<212> TYPE: DNA
<213> ORGANISM: Triticum aestivum
<220> FEATURE:
<221> NAME/KEY: unsure
<222> LOCATION: (401)
<223> OTHER INFORMATION: n=a,c,g or t
<220> FEATURE:
<221> NAME/KEY: unsure
<222> LOCATION: (407)
<223> OTHER INFORMATION: n=a,c,g or t
<220> FEATURE:
<221> NAME/KEY: unsure
<222> LOCATION: (449)
<223> OTHER INFORMATION: n=a,c,g or t
<220> FEATURE:
<221> NAME/KEY: unsure
<222> LOCATION: (456)..(457)
<223> OTHER INFORMATION: n=a,c,g or t
<220> FEATURE:
<221> NAME/KEY: unsure
<222> LOCATION: (493)
<223> OTHER INFORMATION: n=a,c,g or t
<220> FEATURE:
<221> NAME/KEY: unsure
<222> LOCATION: (497)
<223> OTHER INFORMATION: n=a,c,g or t
<220> FEATURE:
<221> NAME/KEY: unsure
<222> LOCATION: (512)
<223> OTHER INFORMATION: n=a,c,g or t

<400> SEQUENCE: 55
gagagatcca agactaggcc ggccggccgg aggagatcga aaggaggag gagacatggt      60 gcgcgggaag ctggaggtgc tgctcgtctc cgccaagggc ctcgacgact ccgatttctt    120
caatagcatg gacccgtacg tgatcctcac ctgccgcagc cacgagcaga agagcaccgt    180
cgcatcagga gcagggagcg agcctgagtg gaacgagacc ttcgtcttcg ccgtctccgg    240
cgacgctccg gagctcaggg tcaagatcat ggacagcgac gccctctcgg ccgacgacct    300
cgtcggagaa gcatgtatcc cgctggaggc tgtgctccag gagggcagcc tgccgccggc    360
cgtgcaccgg gtctcaagga cgaggagtac cgcggggaat naagatngcg ctcacttcac    420
ccggcagagg aaaacaggag gaggaggana ctacgnnggt ggatcatcac tgaaaaggca    480
cgagcacaaa tgngttnttt acgtaaaagg anaaaggttt gat                    523

<210> SEQ ID NO 56
<211> LENGTH: 28
<212> TYPE: PRT
<213> ORGANISM: Triticum aestivum

<400> SEQUENCE: 56

-continued

```
Met Val His Gly Lys Leu Glu Val Leu Leu Val Ser Ala Lys Gly Leu
  1               5                  10                 15

Glu Asp Thr Asp Phe Leu Asn Asn Met Asp Pro Phe
             20                  25
```